(12) United States Patent
Yang et al.

(10) Patent No.: US 12,329,900 B2
(45) Date of Patent: Jun. 17, 2025

(54) INHALATION DEVICE WITH INTEGRATED ELECTRONICS

(71) Applicant: NORTON (WATERFORD) LIMITED, Waterford (IE)

(72) Inventors: Dong Yang, Waterford (IE); Dylan A. Moorhouse, County Wexford (IE)

(73) Assignee: NORTON (WATERFORD) LIMITED, Waterford (IE)

( * ) Notice: Subject to any disclaimer, the term of this patent is extended or adjusted under 35 U.S.C. 154(b) by 614 days.

(21) Appl. No.: 17/583,666

(22) Filed: Jan. 25, 2022

(65) Prior Publication Data

US 2022/0143336 A1    May 12, 2022

Related U.S. Application Data

(63) Continuation of application No. 16/463,838, filed as application No. PCT/EP2017/081452 on Dec. 5, 2017, now Pat. No. 11,266,796.
(Continued)

(51) Int. Cl.
*A61M 15/00* (2006.01)
*A61B 5/00* (2006.01)
(Continued)

(52) U.S. Cl.
CPC ........... *A61M 15/0051* (2014.02); *A61B 5/09* (2013.01); *A61B 5/4833* (2013.01);
(Continued)

(58) Field of Classification Search
CPC .......... A61M 15/0051; A61M 15/0003; A61M 15/008; A61M 15/0026; A61M 15/0073
See application file for complete search history.

(56) References Cited

U.S. PATENT DOCUMENTS

| 5,809,997 A | 9/1998 | Wolf et al. |
| 6,390,088 B1 | 5/2002 | Noehl et al. |

(Continued)

FOREIGN PATENT DOCUMENTS

| CN | 101557852 A | 10/2009 |
| CN | 101883599 A | 11/2010 |

(Continued)

OTHER PUBLICATIONS

Chrystyn, H. , "The Diskus: a review of its position among dry powder inhaler devices", International Journal Clinical Practice, vol. 61, Jun. 2007, 31 pages.
(Continued)

*Primary Examiner* — Margaret M Luarca
(74) *Attorney, Agent, or Firm* — Flaster Greenberg P.C.

(57) ABSTRACT

A device for delivering medication to a user may include a circular or elliptical body that include a mouthpiece, a flexible strip of medication, a lever, and a mouthpiece cover, where the mouthpiece cover is rotatable about the body. The electronics module may include a communication circuit, a sensor system, and a switch. The lever may be configured to actuate the switch when the lever is moved from a closed position to an open position. The lever is configured to advance a dose of medication on the flexible strip when moved from the closed position to the open position. When actuated, the switch may be configured to switch the electronics module from an off state to an active state wen the lever is actuated for a first time by a user. Thereafter, the electronics module is configured to not return to the off state.

20 Claims, 15 Drawing Sheets

Related U.S. Application Data

(60) Provisional application No. 62/430,576, filed on Dec. 6, 2016.

(51) Int. Cl.
  *A61B 5/09* (2006.01)
  *A61B 5/087* (2006.01)
  *A61M 16/00* (2006.01)

(52) U.S. Cl.
  CPC .... *A61M 15/0003* (2014.02); *A61M 15/0021* (2014.02); *A61M 15/008* (2014.02); *A61B 5/0871* (2013.01); *A61B 5/7267* (2013.01); *A61B 2562/0204* (2013.01); *A61M 15/0026* (2014.02); *A61M 15/0073* (2014.02); *A61M 2016/0024* (2013.01); *A61M 2016/0039* (2013.01); *A61M 2202/064* (2013.01); *A61M 2205/3344* (2013.01); *A61M 2205/3553* (2013.01); *A61M 2205/3584* (2013.01); *A61M 2205/52* (2013.01); *A61M 2205/587* (2013.01); *A61M 2205/8206* (2013.01); *A61M 2205/8212* (2013.01)

(56) References Cited

U.S. PATENT DOCUMENTS

| | | |
|---|---|---|
| 6,958,691 B1 | 10/2005 | Robertson et al. |
| 6,990,975 B1 | 1/2006 | Jones et al. |
| 7,072,738 B2 | 7/2006 | Robertson et al. |
| 7,151,456 B2 | 12/2006 | Godfrey et al. |
| 7,191,777 B2 | 3/2007 | Brand et al. |
| 7,198,172 B2 | 4/2007 | Lintell et al. |
| 7,233,228 B2 | 6/2007 | Lintell et al. |
| 7,249,687 B2 | 7/2007 | Anderson |
| 7,347,200 B2 | 3/2008 | Jones et al. |
| 7,383,837 B2 | 6/2008 | Robertson et al. |
| 7,424,888 B2 | 9/2008 | Lintell et al. |
| 7,495,546 B2 | 2/2009 | Lintell |
| 7,837,648 B2 | 11/2010 | Blair et al. |
| 8,201,556 B2 | 6/2012 | Jones et al. |
| 8,240,301 B2 | 8/2012 | Spaargaren et al. |
| 8,408,201 B2 | 4/2013 | Pocock et al. |
| 8,511,304 B2 | 8/2013 | Anderson et al. |
| 8,746,243 B2 | 6/2014 | Kirniak |
| 8,931,480 B2 | 1/2015 | Meliniotis et al. |
| 9,289,565 B2 | 3/2016 | Briant et al. |
| 9,782,550 B2 | 10/2017 | Morrison et al. |
| 10,183,133 B2 | 1/2019 | Meliniotis et al. |
| 2001/0025639 A1 | 10/2001 | Soren et al. |
| 2002/0000225 A1 | 1/2002 | Schuler et al. |
| 2003/0163099 A1 | 8/2003 | Wermeling et al. |
| 2004/0089299 A1 | 5/2004 | Bonney et al. |
| 2004/0117062 A1 | 6/2004 | Bonney et al. |
| 2005/0066961 A1 | 4/2005 | Rand |
| 2005/0119604 A1 | 6/2005 | Bonney et al. |
| 2005/0154491 A1* | 7/2005 | Anderson ............ A61M 15/00 700/236 |
| 2005/0161467 A1 | 7/2005 | Jones et al. |
| 2005/0174216 A1 | 8/2005 | Lintell et al. |
| 2005/0178382 A1 | 8/2005 | Riley et al. |
| 2005/0247312 A1 | 11/2005 | Davies et al. |
| 2005/0251289 A1 | 11/2005 | Bonney et al. |
| 2005/0268909 A1 | 12/2005 | Bonney et al. |
| 2005/0274378 A1 | 12/2005 | Bonney et al. |
| 2006/0130838 A1* | 6/2006 | Lee ............... A61B 5/087 128/200.23 |
| 2006/0243275 A1 | 11/2006 | Ruckdeschel et al. |
| 2008/0178872 A1 | 7/2008 | Genova et al. |
| 2010/0250280 A1 | 9/2010 | Sutherland et al. |
| 2013/0269685 A1 | 10/2013 | Jung et al. |
| 2014/0053833 A1 | 2/2014 | Cline et al. |
| 2014/0261443 A1 | 9/2014 | Lowenstein et al. |
| 2015/0231343 A1* | 8/2015 | Reilly ............... A61B 7/003 128/202.22 |
| 2016/0256639 A1 | 9/2016 | Van Sickle et al. |
| 2016/0325057 A1 | 11/2016 | Morrison et al. |
| 2018/0140786 A1 | 5/2018 | Calderon Oliveras et al. |

FOREIGN PATENT DOCUMENTS

| | | |
|---|---|---|
| CN | 102176940 A | 9/2011 |
| CN | 103429288 A | 12/2013 |
| CN | 104507521 A | 4/2015 |
| GB | 2506385 A | 4/2014 |
| JP | 2002526210 A | 8/2002 |
| JP | 2005511257 A | 4/2005 |
| JP | 2005533585 A | 11/2005 |
| JP | 2016515410 A | 5/2016 |
| JP | 2020501855 A | 1/2020 |
| KR | 20080005992 A | 1/2008 |
| WO | 0016836 A1 | 3/2000 |
| WO | 03051438 A1 | 6/2003 |
| WO | 03063754 A1 | 8/2003 |
| WO | 2004011070 A1 | 2/2004 |
| WO | 2004011071 A1 | 2/2004 |
| WO | 2005014089 A1 | 2/2005 |
| WO | 2005/084737 A1 | 9/2005 |
| WO | 2005533584 A | 11/2005 |
| WO | 2008070516 A2 | 6/2008 |
| WO | 2009003989 A1 | 1/2009 |
| WO | 2011157561 A1 | 12/2011 |
| WO | 2014033229 A1 | 3/2014 |
| WO | 2014145411 A2 | 9/2014 |
| WO | 2014147550 A1 | 9/2014 |
| WO | 2014204511 A2 | 12/2014 |
| WO | 2015031472 A1 | 3/2015 |
| WO | 2015178907 A1 | 11/2015 |
| WO | 2016/043601 A1 | 3/2016 |
| WO | 2016030521 A1 | 3/2016 |
| WO | 2016033419 A1 | 3/2016 |
| WO | 2016033421 A1 | 3/2016 |
| WO | 2016081294 A1 | 5/2016 |
| WO | 2016111633 A1 | 7/2016 |
| WO | 2018104268 A1 | 6/2018 |

OTHER PUBLICATIONS

Grant, Andrew, et al., "The ELLIPTA Dry Powder Inhaler: Design, Functionality, In Vitro Dosing Performance and Critical Task Compliance by Patients ad Caregivers", Journal of Aerosol Medicine & Pulmonary Drug Delivery, vol. 28, Nov. 30, 2015, 13 pages.

* cited by examiner

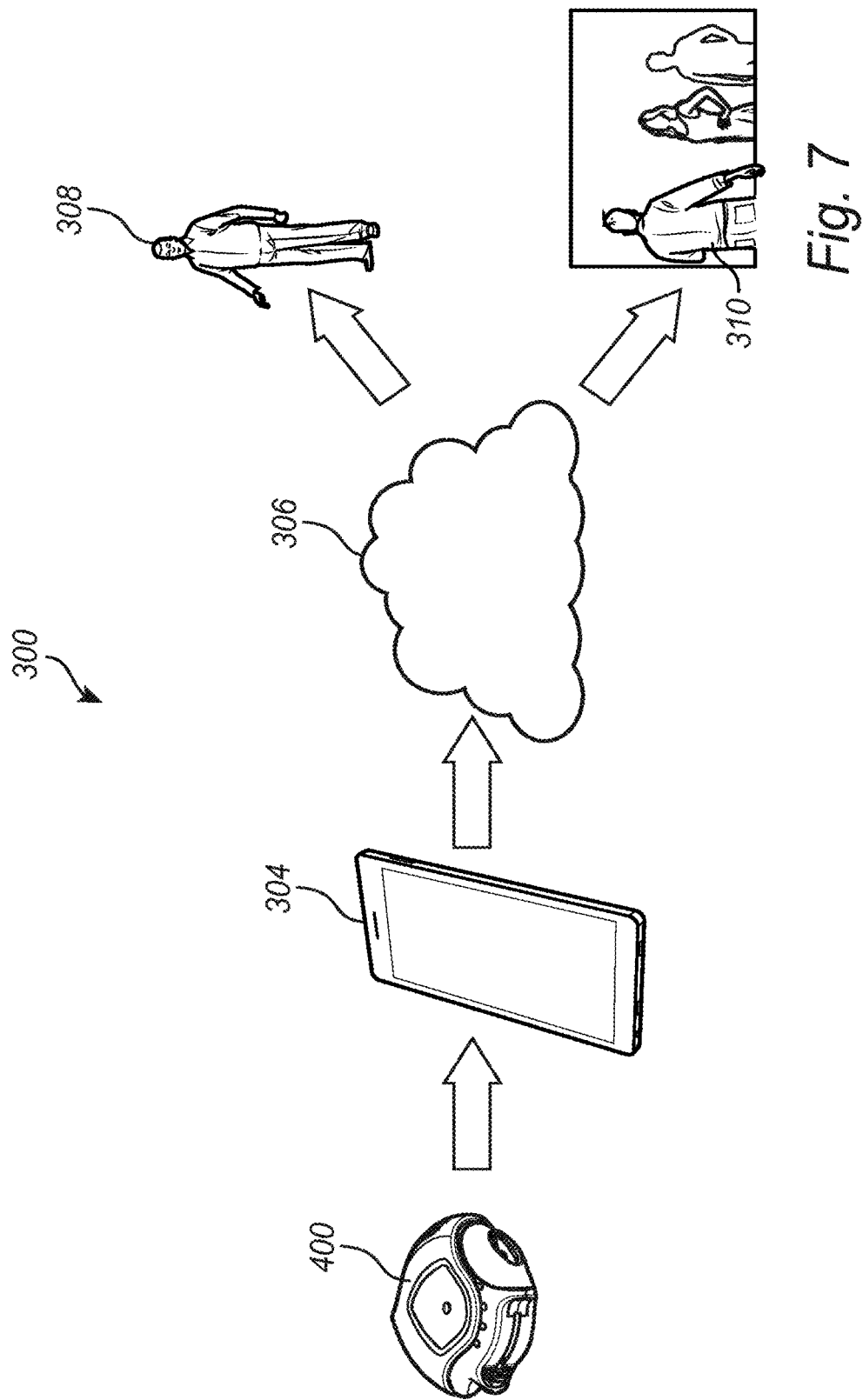

INHALATION DEVICE WITH INTEGRATED ELECTRONICS

CROSS-REFERENCE TO RELATED APPLICATIONS

This application is a continuation of U.S. patent application Ser. No. 16/463,838, filed May 23, 2019, which is the National Stage Entry under 35 U.S.C. § 371 of Patent Cooperation Treaty Application No. PCT/EP2017/081452, filed Dec. 5, 2017, which claims the benefit of Provisional U.S. Patent Application No. 62/430,576, filed Dec. 6, 2016, the disclosure of which is incorporated herein by reference in its entirety.

BACKGROUND

Drug delivery devices facilitate the delivery of medication into a patient's body via various routes of administration. Typical routes of administration include oral, topical, sub-lingual inhalation, injection and the like. The devices may be used to deliver medications for the treatment various diseases, ailments and medical conditions. Inhalation devices, for example, may be used to treat asthma, chronic obstructive pulmonary disease (COPD) and cystic fibrosis (CF). While drug delivery devices are designed to deliver an appropriate dose of medication to a patient as part of a therapeutic treatment, the effectiveness of a particular treatment may be influenced by non-physiological factors, such as the patient's adherence and compliance.

In the context of a drug therapy, adherence may refer to the degree to which a patient is following a prescribed dosing regimen. For example, if the patient's prescription calls for two doses each day, and the patient is taking two doses per day, the patient may be considered 100% adherent. If the patient is only taking one dose per day, he or she may be deemed only 50% adherent. In the latter case, the patient may not be receiving the treatment prescribed by his or her doctor, which may negatively affect the efficacy of the therapeutic treatment.

Compliance may refer to a patient's technique when using a particular drug delivery device. If the patient is using the device in a manner that is recommended by a doctor or by a manufacturer, the device is likely to deliver the desired dose of medication and the patient may be deemed compliant. However, if the device is not being used properly during drug administration, the device's ability to deliver a proper dose of medication may be compromised. As such, the patient may be deemed non-compliant. In the case of an inhalation device, for example, the patient may need to achieve a minimum inspiratory effort to ensure a full dose of medication is delivered from the device into the patient's lungs. For some patients, such as children and the elderly, meeting the requirements for full compliance may be difficult due to physical limitations, such as limited lung function. Accordingly, like adherence, failing to achieve full compliance may reduce the effectiveness of a prescribed treatment.

A patient's ability to achieve full compliance may be further complicated by certain physical properties of the medication. For example, some respiratory medications may consist of fine particles and/or may lack any odor or taste. Thus, a patient using an inhalation device may not be able to correct a non-compliant use because he or she may not be able to immediately detect or sense that medication is being inhaled and/or know whether the amount of inhaled medication complies with the prescription.

SUMMARY

A drug delivery device may be adapted to include an electronics module that is configured to sense, track, and/or process usage conditions and parameters associated with the device (e.g., to improve adherence and compliance). The electronics module may be further configured to communicate the conditions and parameters to external devices, such as a smartphone, for similar and/or further processing. The inclusion of an electronics module in a drug delivery device opens the doors to a wealth of digital improvements and features to enhance the use of the device. The electronics module, in this context, may create a platform to leverage helpful smartphone applications and powerful data analytics. However, the introduction of electronics into any drug delivery device may introduce certain technical challenges, such as durability, reliability, electro-mechanical integration, power management, and drug delivery performance. The present disclosure provides solutions for inclusion of certain electrical components with a drug delivery device, such as an inhaler.

Examples of inhalation devices (e.g., breath-actuated inhalers) are provided herein. The inhalation device may include a body (e.g., a circular body) and electronics for an electronics module. The body may include a mouthpiece, one or more flexible strips of medication (e.g., a blister strip), a lever, and a mouthpiece cover rotatable about the body. Rotating the mouthpiece cover from a closed position to an open position may expose the mouthpiece, and may also expose the lever for actuation by a user. Actuation of the lever from a closed position to an open position may advance the flexible strip of medication to prepare a dose of medication for delivery to the user and/or may expose a powder outlet so that a blister of medication is in fluid communication with the mouthpiece (e.g., for delivery to the user). The electronics module may include a controller, a communication circuit, a sensor system, a switch, a power source, and a memory. The lever may be configured to actuate the switch (e.g., compress the switch) when the lever moves from a first position (e.g., an open position) to a second position (e.g., a closed position), and/or actuate the switch (e.g., decompress the switch) when the lever moves from the second position (e.g., the closed position) to the first position (e.g., the open position). When actuated by the lever, the switch may provide a signal to the controller that may be indicative of the position of the lever and/or the preparation of a dose of medication for the user. The signal may be timestamped and stored in memory. The controller and the switch may also be configured to cause the electronics module to switch or transition between power states, which may be used to manage power consumption from the power source.

When the lever is moved from the first position to the second position for the first time by a user (e.g., after purchase and before the first use of the device by the user), the lever is configured to engage the switch, causing the electronics module to transition from the off state to an active state and to sense an inhalation by the user from the mouthpiece. Thereafter, the electronics module may be configured to not return to the off state after the lever is moved to from the first position to the second position for the first time by the user (e.g., the inhalation device may never return to the off state again throughout its lifecycle). The electronics module may be configured to start an internal counter when transitioning from the off state. The electronics module may be configured to timestamp a sensed inhalation or movement of the lever based on the internal counter.

The lever may be configured to advance a dose of medication on the flexible strip when the lever is moved from the first position to the second position. Further, in some examples, the body may include a mouthpiece cover, and the lever may be part of the mouthpiece cover. For example, the lever may be configured to move from the first position to the second position when the mouthpiece cover is moved from a closed position to an open position to expose the mouthpiece. Additionally, in some examples, the body may include more than one flexible strip of medication, where each flexible strip may include different medication. Accordingly, in such examples, the lever may be configured to advance multiple flexible strips when the lever moves from the first position to the second position so that medication from each of the flexible strips are made available to the user through the mouthpiece.

When the electronics module is in the active state, the electronics module may be configured to perform at least one of the following: measure one or more atmospheric pressures within the inhaler after the lever is moved from the first position to the second position; determine inhalation parameters based on the at least one measured atmospheric pressures; store the inhalation parameters in a local memory; advertise to an external device; and transmit the inhalation parameters to the external device. The electronics module may be configured to be in a sleep state when not in the off state or the active state. The electronics module may be configured to change from the active state to the sleep state upon the electronics module determining that one or more atmospheric pressure measurements received from a pressure sensor do not fall within the predetermined range for a predetermined amount of time, the predetermined amount of time based on the internal counter. The electronics module may be configured to store a timeout event and associated timestamp when the lever is moved from the first position to the second position and the one or more atmospheric pressure measurements are not within the predetermined range within the predetermined amount of time.

The sensor system of the electronics module may include a pressure sensor that may measure at least one atmospheric pressure within the inhaler after the lever is moved from the first position to the second position. The pressure sensor may be configured to take measurements for a predetermined period of time or until a predetermined event is detected. The electronics module may include a processor configured to determine one or more inhalation parameters (e.g., airflow metrics) based on the at least one measured atmospheric pressures.

The inhalation parameters may include peak flow rate, average flow rate, a time to peak flow rate, an inhaled volume, an inhalation duration etc. The inhalation parameters may be indicative of the quality or strength of a user's inhalation and, thus, the extent to which a full dose of medication has been delivered. The inhalation parameters may also be indicative of a patient's technique when using the inhalation device. For example, the inhalation parameters may indicate whether the patient is inhaling from or exhaling into the device and/or whether portions of the flow pathway are blocked or obstructed. The inhalation parameters may be timestamped and stored in memory. The electronics module may be configured to communicate to an external device, such as a smartphone, some or all of the data that has been generated, processed and/or stored by the electronics module. The external device may include software for processing the received data and for displaying, among other things, information indicative of a user's compliance and/or adherence with respect to the inhalation device.

BRIEF DESCRIPTION OF THE DRAWINGS

FIG. 7 is a diagram of an example system including the inhalation device of FIG. 1A.

DETAILED DESCRIPTION

The present disclosure describes devices, systems and methods for sensing, tracking and/or processing usage conditions and parameters associated with a drug delivery device. The devices, systems and methods are described in the context of a breath-actuated inhalation device for delivering medication into a user's lungs. However, the described solutions are equally applicable to other drug delivery devices, such as an injector, a metered-dose inhaler, a nebulizer, a transdermal patch, or an implantable.

Figure 1A:
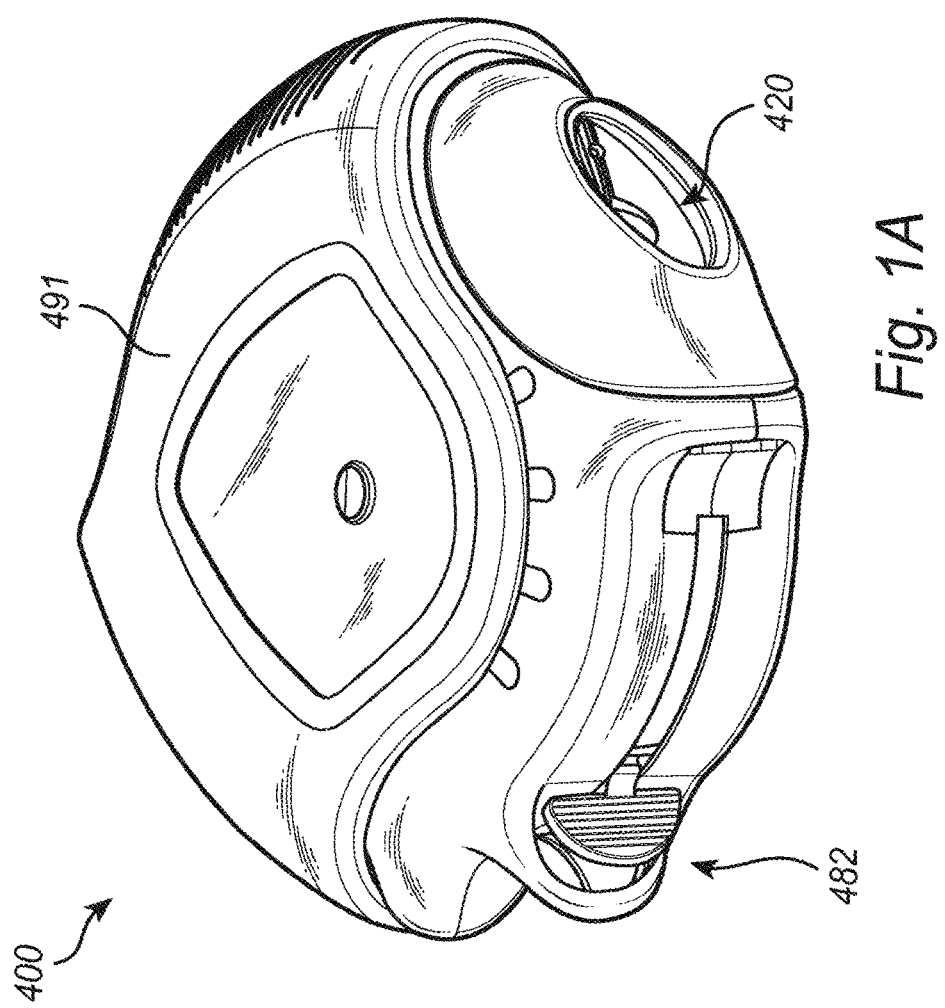
FIG. 1A is a perspective view of an example inhalation device.
Figure 1B:
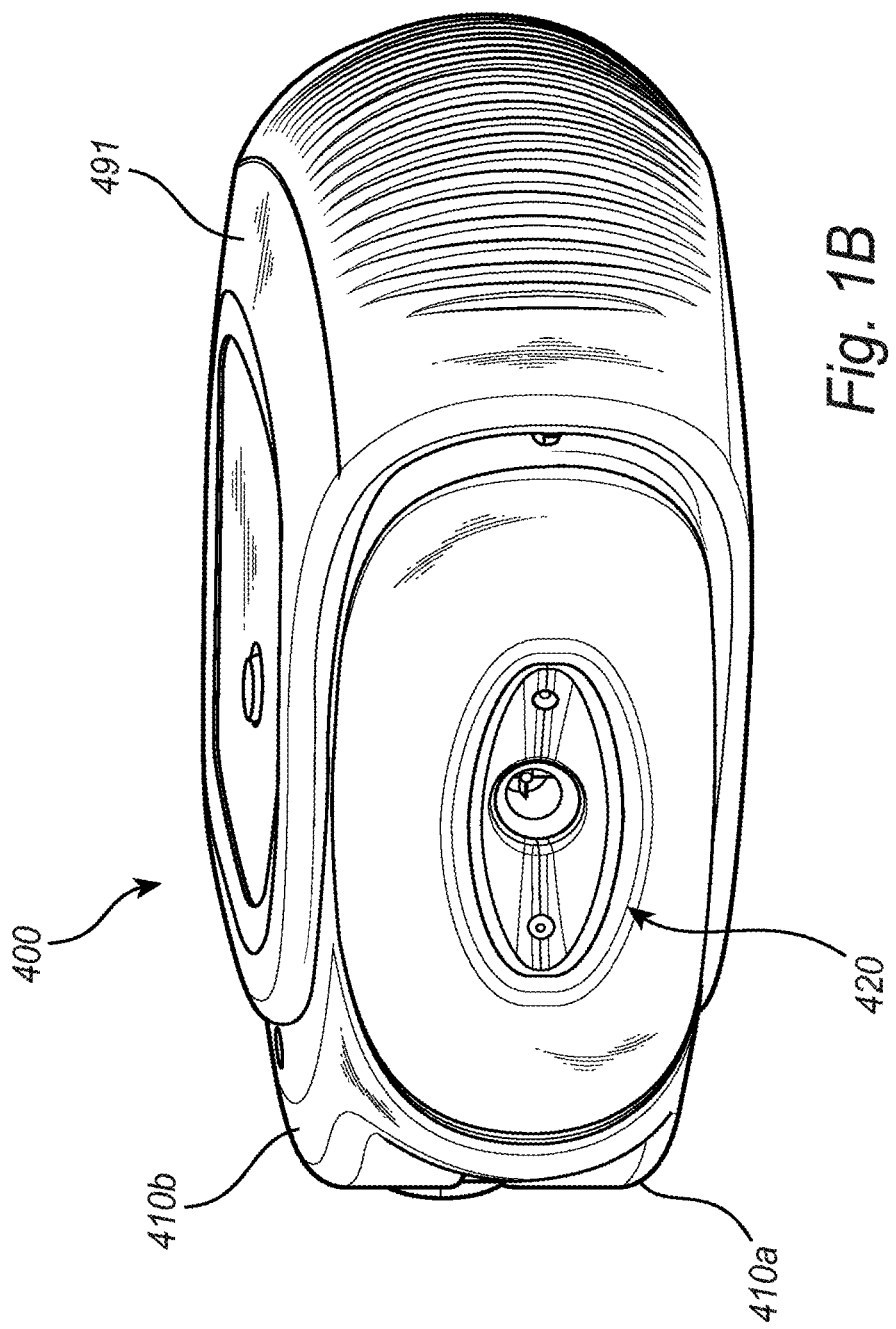
FIG. 1B is a front perspective view of the example inhalation device of FIG. 1A.
Figure 2A:
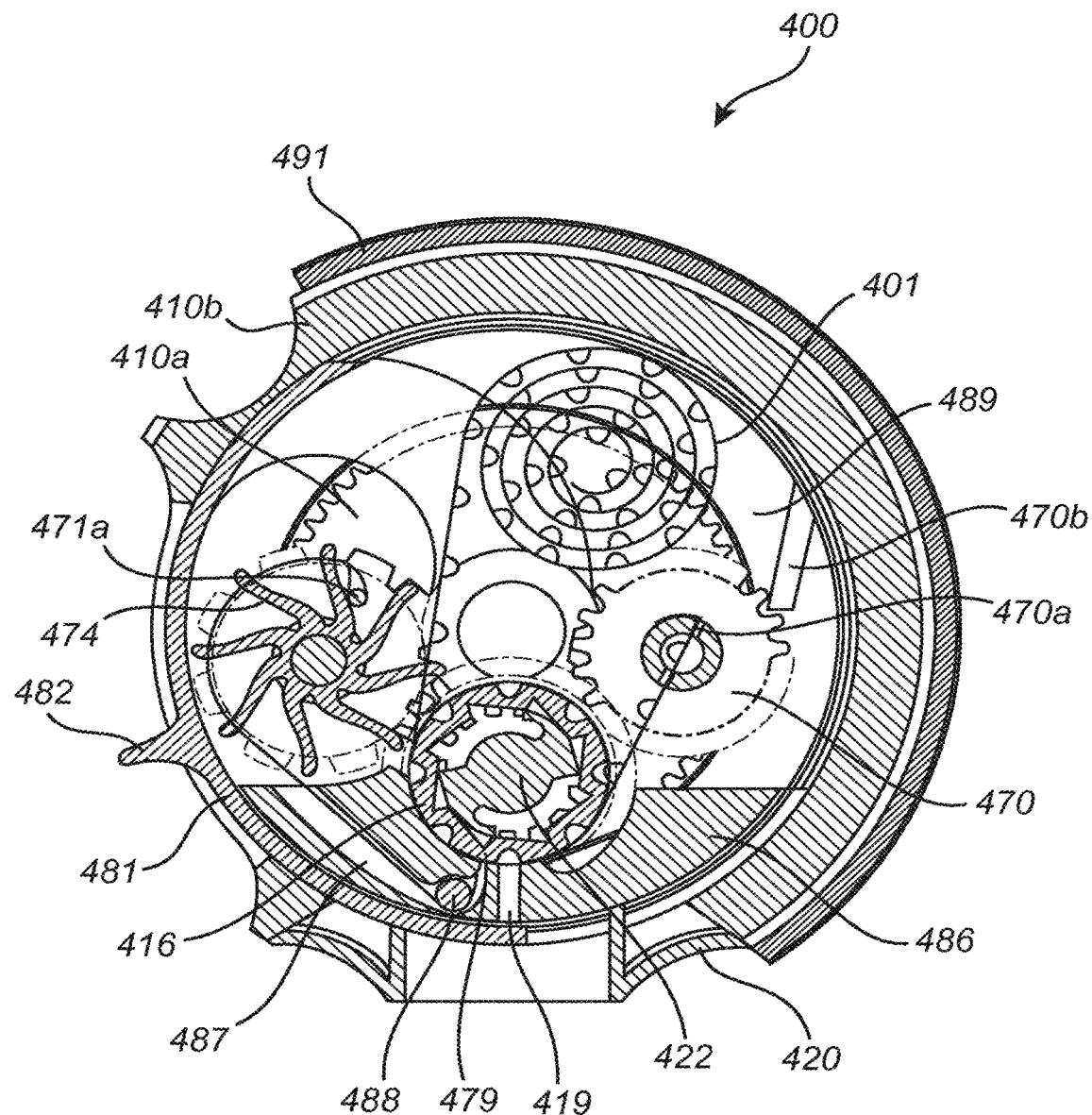
FIG. 2A is a cross-sectional interior view of the example inhalation device of FIG. 1A.
Figure 2B:
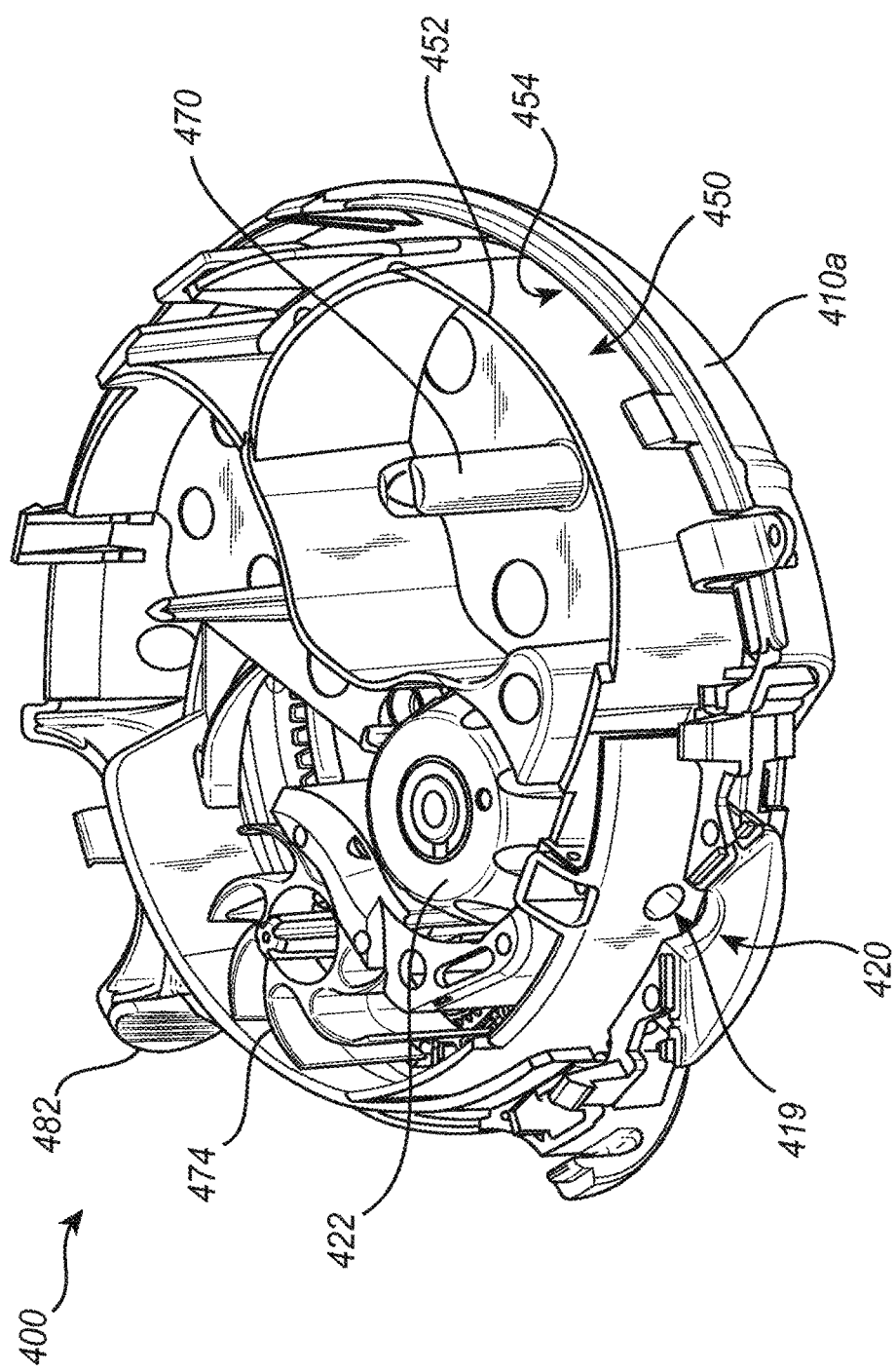
FIG. 2B is a cross-sectional interior perspective view of the example inhalation device of FIG. 1A.

FIG. 1A is a perspective view of an example inhalation device 400. FIG. 1B is a front perspective view of the example inhalation device 400. FIG. 2A is a cross-sectional interior view of the example inhalation device 400. FIG. 2B is a cross-sectional interior perspective view of the example inhalation device 400 without a flexible strip 401 installed inside. FIGS. 3A-D are perspective views of the inhalation device 400 as a cover 491 is moved from a closed position to an open position. FIG. 4 is an exploded perspective view of the example inhalation device 400.

The inhalation device 400 may include the flexible strip 401 that is mounted inside the inhalation device 400. The flexible strip 401 may define a plurality of pockets 402, each of which containing a dose of medicament which can be inhaled, in the form of a powder. The strip 401 may include a base sheet 403 in which blisters are formed to define the pockets 402, and a lid sheet 404 which is hermetically sealed to the base sheet 403 except in the region of the blisters, in such a manner that the lid sheet and the base sheet can be peeled apart. The sheets are sealed to one another over their whole width except for leading end portions thereof where they are preferably not sealed to one another at all. The lid and base sheets are each preferably formed of a plastics/aluminium laminate, and the lid and base sheets are preferably adhered to one another by heat sealing. By way of example, the lid material may be a laminate consisting of 50 gsm bleach kraftpaper/12 micron polyester (PETP) film/20 micron soft temper aluminium foil/9 gsm vinylic peelable heat seal lacquer (sealable to PVC), and the base material may be a laminate consisting of 100 micron PVC/45 micron soft temper aluminium foil/25 micron orientated polyamide. The lacquer of the lid material is sealed to the PVC layer of the base material to provide the peelable seal between the lid and base sheets.

The strip 401 may include elongate pockets which run transversely with respect to the length of the strip. Elongated pockets may enables a large number of pockets to be provided in a given strip length. The strip may, for example, be provided with sixty or one hundred pockets, but it will be understood that the strip may have any suitable number of pockets.

The inhalation device 400 is configured to receive the flexible strip 401. The lid sheet 404 has a loop 404a formed at the leading end thereof for engagement over a post 471a extending upwardly from a toothed wheel 471. The base sheet has a lead portion 403a of reduced width for engagement in a slot 470a formed in the base winding wheel 470. The leading end portions of the base sheet and lid sheet may not be sealed together.

The inhalation device 400 may include a body 410. The body 410 may include a base 410a and a top 410b both of generally circular shape. When the device 400 is assembled the base and top are snap-fitted together. The body defines a single internal chamber within which the strip 401 is housed and within which are also housed a wheel 414 for winding up the used portion of the lid sheet 404, a base winding wheel 470, and an index wheel 416 (e.g., and an electronics module, as described herein). The index wheel 416 is hollow and an index ratchet wheel 422 is housed within it. All the wheels may be mounted in the chamber defined by the body, for rotational movement with respect thereto. A pawl 470b is attached to the body 410 and engages the teeth of the base winding wheel 470 to prevent the wheel moving anticlockwise, thus ensuring that the strip 401 can only proceed forwards through the device.

The lid winding wheel 414 may be formed in two parts, namely a toothed wheel 471 having teeth 472 and a shaft 473, and a collapsible wheel 474 having a hollow central shaft 475 and a plurality of resilient arms 476, for example, as shown, eight such arms, extending from the central shaft 475 each at an angle to a radius. The toothed wheel 471 has a lug 477 that may engage in a corresponding notch in the shaft 475 so that the wheels 471 and 474 rotate in unison. The hollow index wheel 416 has external teeth 478 which mesh with the teeth of the base winding wheel 470 and the teeth of the wheel 471. Ratchet teeth 479 are formed on the internal walls of the index wheel 416, and the index ratchet wheel 422 has two pawls 480 which engage the ratchet teeth 479.

The inhalation device 400 may include a manifold 486. The manifold 486 may provide communication between the chamber within the body 410 and a mouthpiece 420. The manifold 486 may include a powder outlet 419 and a passageway 487, for example, to allow used lid strip 404 to pass to the collapsible wheel 474. The powder outlet 419 may provide for fluid communication between the mouthpiece 420 and a dose of medication on the flexible strip 401 (e.g., so that a user may inhale the dose of medication through the mouthpiece 420 ). A roller 488 may be provided to guide the strip 404 into the passageway 487.

The inhalation device 400 may also include a lever 424. The lever 424 may define an arcuate wall 481 with a finger tab 482, and an arm 483 which extends inwardly from the wall 481 and carries an arcuate array of teeth 484 at its distal end. The lever 424 may be pivotally mounted to the center of the base 410a for movement about an axis which is at the center of the pitch circle of the teeth 484, the teeth 484 mesh with the teeth 485 on the index ratchet wheel 422. The lever 424 may be configured to be in a "closed" position, prior to actuation of the lever 424 where the arcuate wall 481 covers the powder outlet 419, and in an "open" position, after actuation of the lever 424 where the actuate wall 481 no longer covers the powder outlet 419 and/or where the flexible strip 401 is advanced so that a dose of medication is prepared for delivery to the user.

The inhalation device may include a dose monitor ring 489 having teeth 490. The dose monitor ring 489 may be arranged to be rotatable within the body base 410a. On its lower surface this bears indicia (not visible in the drawings), which can be viewed by the user through a window 494 in the body 410. The window can be seen both when the cover 491 is closed and when it is open. The indicia indicate either exactly or approximately the number of doses left (e.g., or the number of doses used). The ring 489 is rotated by virtue of the fact that its teeth 490 are engaged by the teeth 478 of the index wheel.

The inhalation device 400 may comprise a cover 491. The cover 491 may be pivotally mounted on the body 410 by means of a lug 492 on the body top 410b and a corresponding lug 493 on the body base 410a. The cover 491 may be pivotal between an open position in which the mouthpiece is exposed and a closed position in which it is not, as is described herein. Further, moving the cover 491 from the closed position to the open position may expose the lever 424 for actuation by the user. The cover 491 may be rotatable about a peripheral of the body 410, where the body 410 may be circular or elliptical in shape.

Actuation of the lever 424 may advance the flexible strip 401 and prepare a dose of medication for the user. For example, in operation, the user may move the cover 491 to its open position and then presses on the finger tab 482 of the lever 424 (e.g., actuate the lever 424) to cause the lever 424 to move as the lever 424 pivots. The actuation of the lever 424 makes the index ratchet wheel 422 rotate which, via the pawls 480, causes the index wheel 416 also to rotate. Rotation of the index wheel 416 produces rotation of both the base winding wheel 470 and the lid winding wheel 414, thus peeling the base sheet and lid sheet apart over a distance sufficient to expose a previously unopened pocket 402 opposite the end of the powder outlet 419 in the manifold 486. The patient can then inhale through the mouthpiece 420.

Figure 3A:
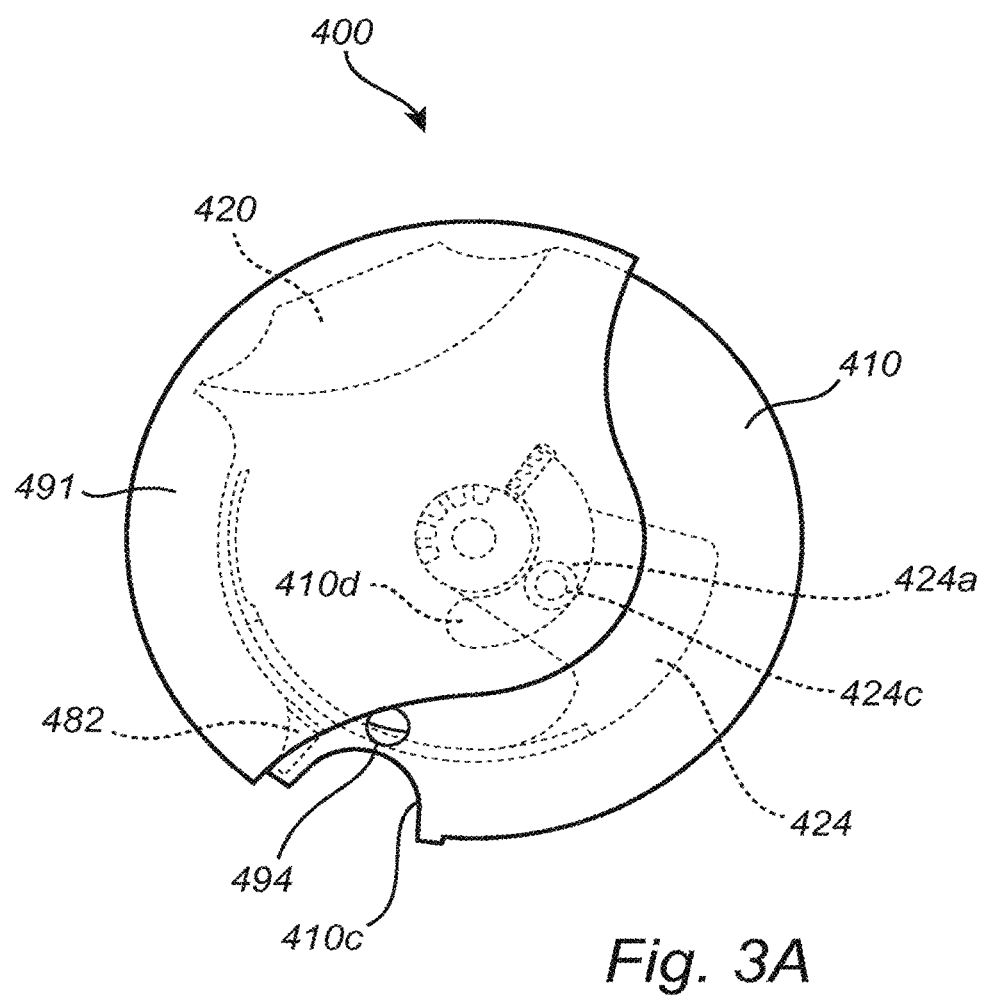
FIG. 3A-D are perspective views of the inhalation device of FIG. 1A as a cover is moved from a closed position to an open position.
Figure 3B:
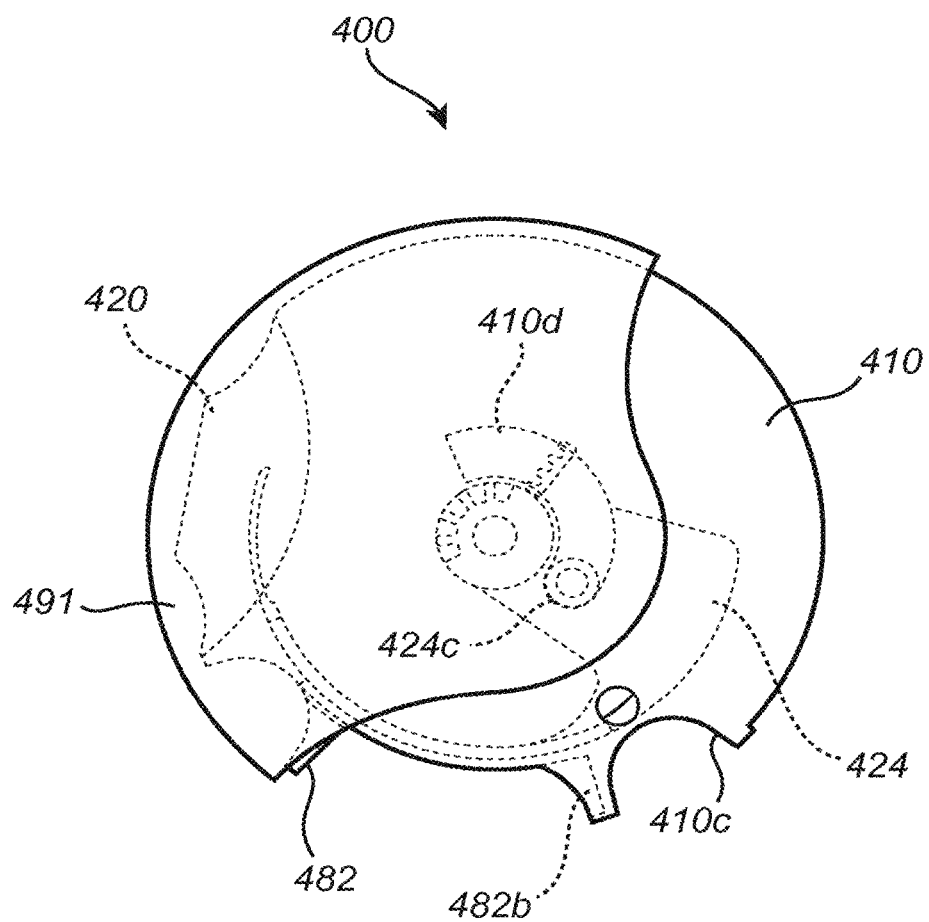

Successive stages in the operation of the device are shown in FIGS. 3A to 3D. The inhalation device 400 may be in its closed position in FIG. 3A. The finger tab 482 of the lever 424 is at this stage in a recess 482b formed in the body 410 (e.g., which may be seen more clearly in FIGS. 3B and 3C). The cover 419 may be held stationary as the body 410 is rotated counter-clockwise, a recess 410c being provided in the periphery of the body to enable the user to insert a finger for this purpose. The device 400 is thus moved to the partly open position shown in FIG. 3B. During this process the lever 424 remains stationary with respect to the cover 491. This is achieved by the lever 424 being provided internally with a resilient arm 424a the tip 424b of which engages in a recess 491a in the cover 491. The arm 424a is attached to the lever 424 via a cylindrical member 424c. As viewed in FIG. 3A, the arm 424a extends anticlockwise from the member 424c over an arc of about 90°. The cylindrical member 424c is guided in an arcuate slot 410d formed in the body 410. The slot 410d extends through an arc of about 180°, and in FIG. 3A the member 424c is shown as being approximately half way along its length. In FIG. 3B it is shown as being at one end.

Figure 3C:
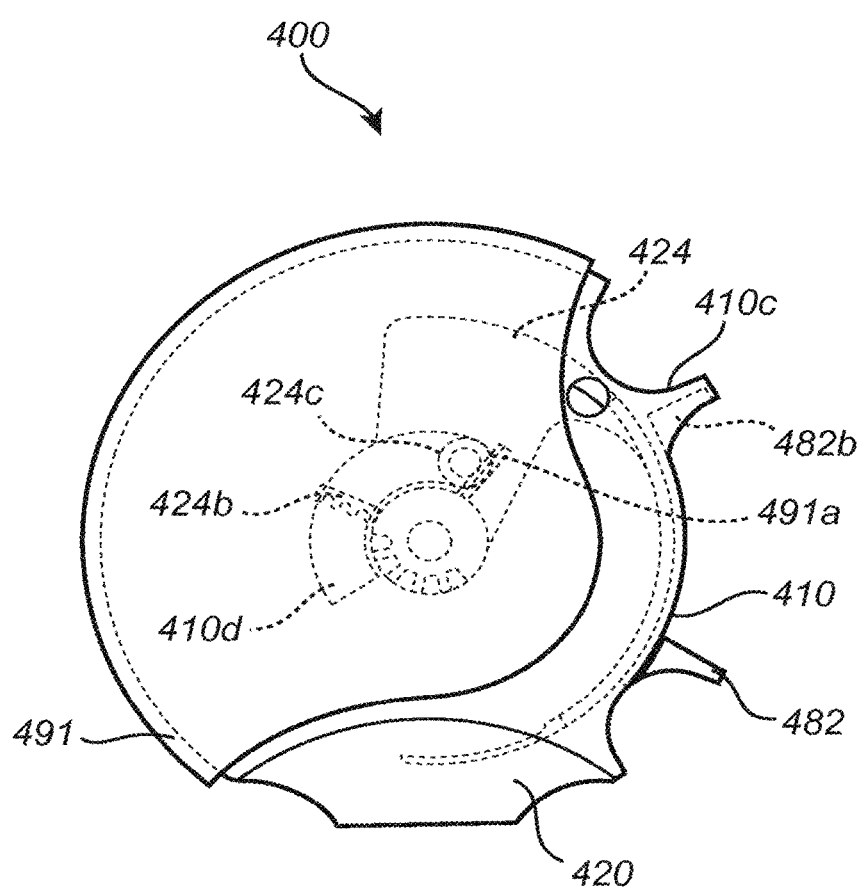
Figure 3D:
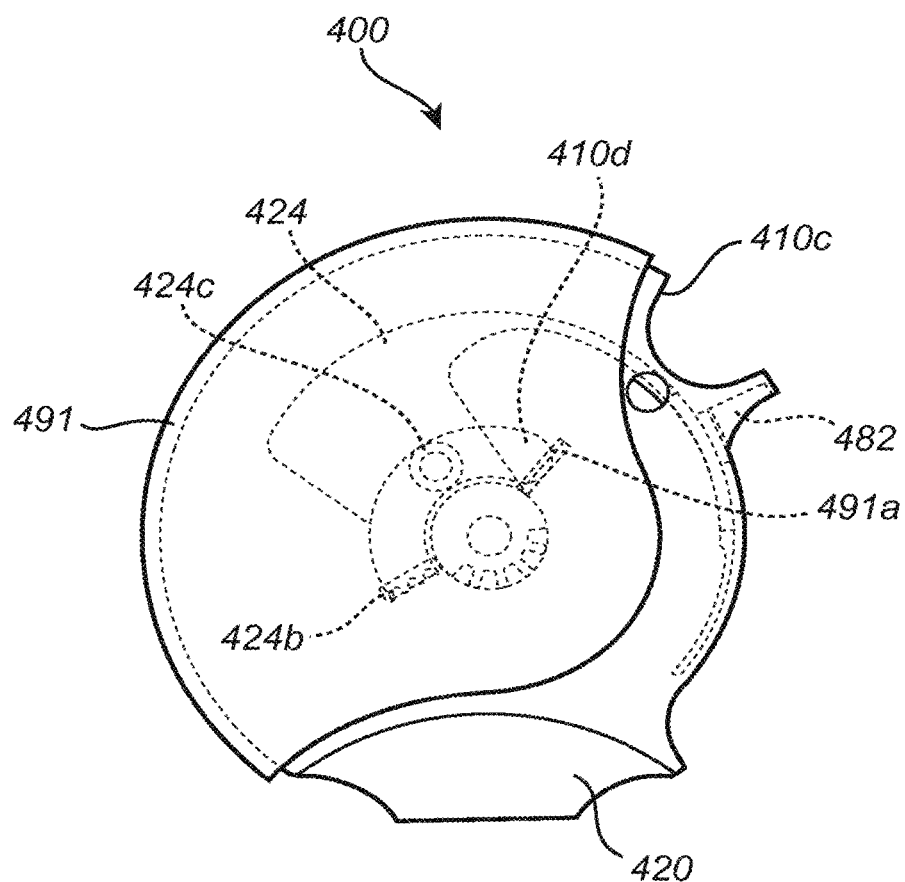
Figure 4:
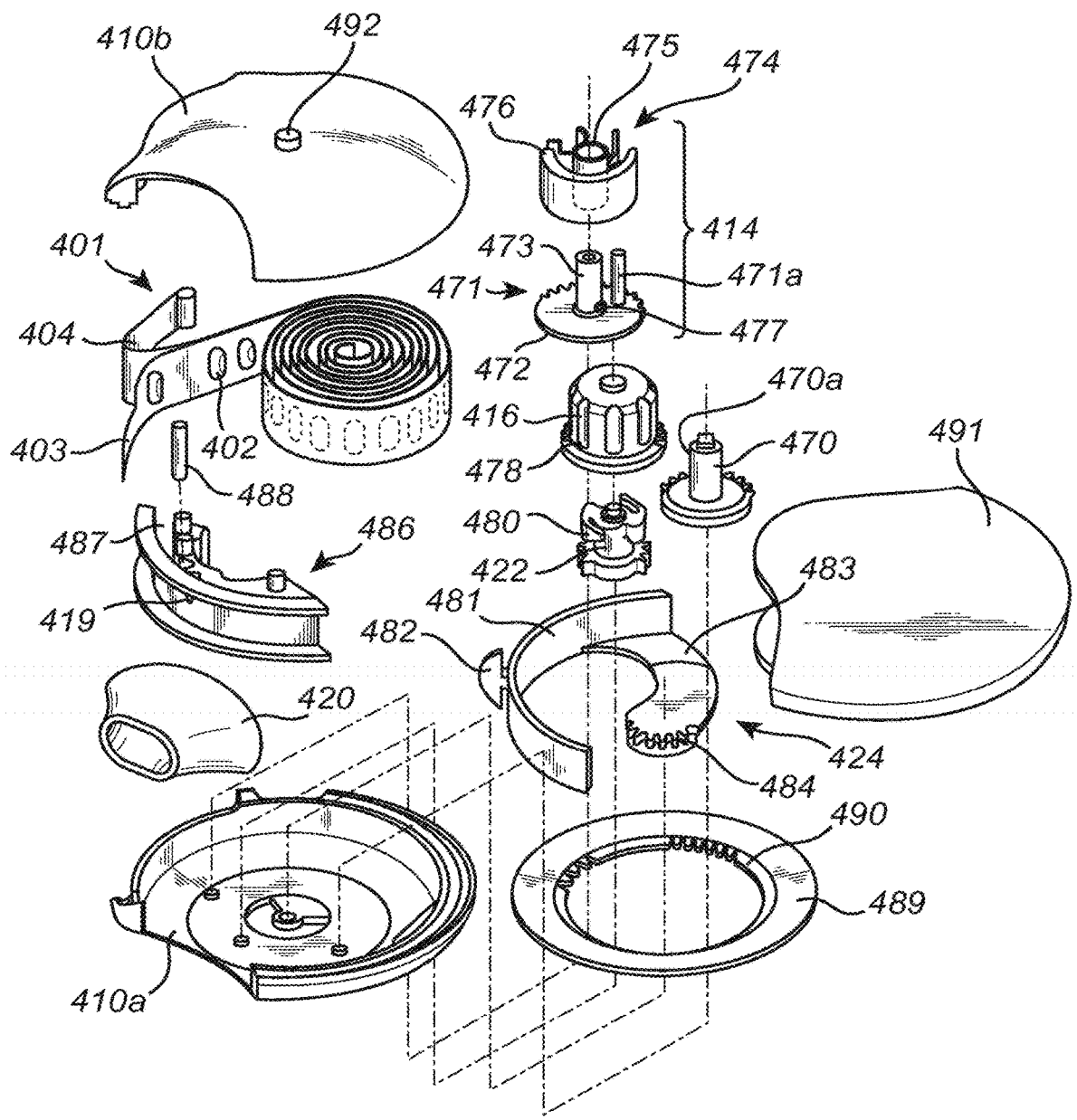
FIG. 4 is an exploded perspective view of the example inhalation device of FIG. 1A.

The user may continue to rotate the body 410 from the position shown in FIG. 3B to the position shown in FIG. 3C. During this further rotation tip 424b of the arm 424a jumps out of the recess 491a. This occurs because, with the member 424c at one end of the slot 410d, movement of the body 410 carries the member 424c with it in an anticlockwise direction and hence compels the arm 424a likewise to move anticlockwise. The user then moves the lever 424 by pushing on the finger tab 482 to cause it to rotate anticlockwise through the position shown in FIG. 3C to the position shown in FIG. 3D where the finger tab 482 re-enters the recess 482b. The steps thus far described both expose the mouthpiece 420 and open a fresh blister on the flexible strip 401. The device 400 is therefore now ready for the user to inhale. After use, the body 410 is rotated clockwise, the lever 424 moving in unison with the body, to bring the device back to the position of FIG. 3A.

As more of the lid sheet is wound onto the wheel 474, the arms 476 may gradually flex inwardly, and the effect is to keep the external diameter of the reel of wound up lid sheet substantially constant, while the internal diameter thereof gradually decreases.

Figure 5:
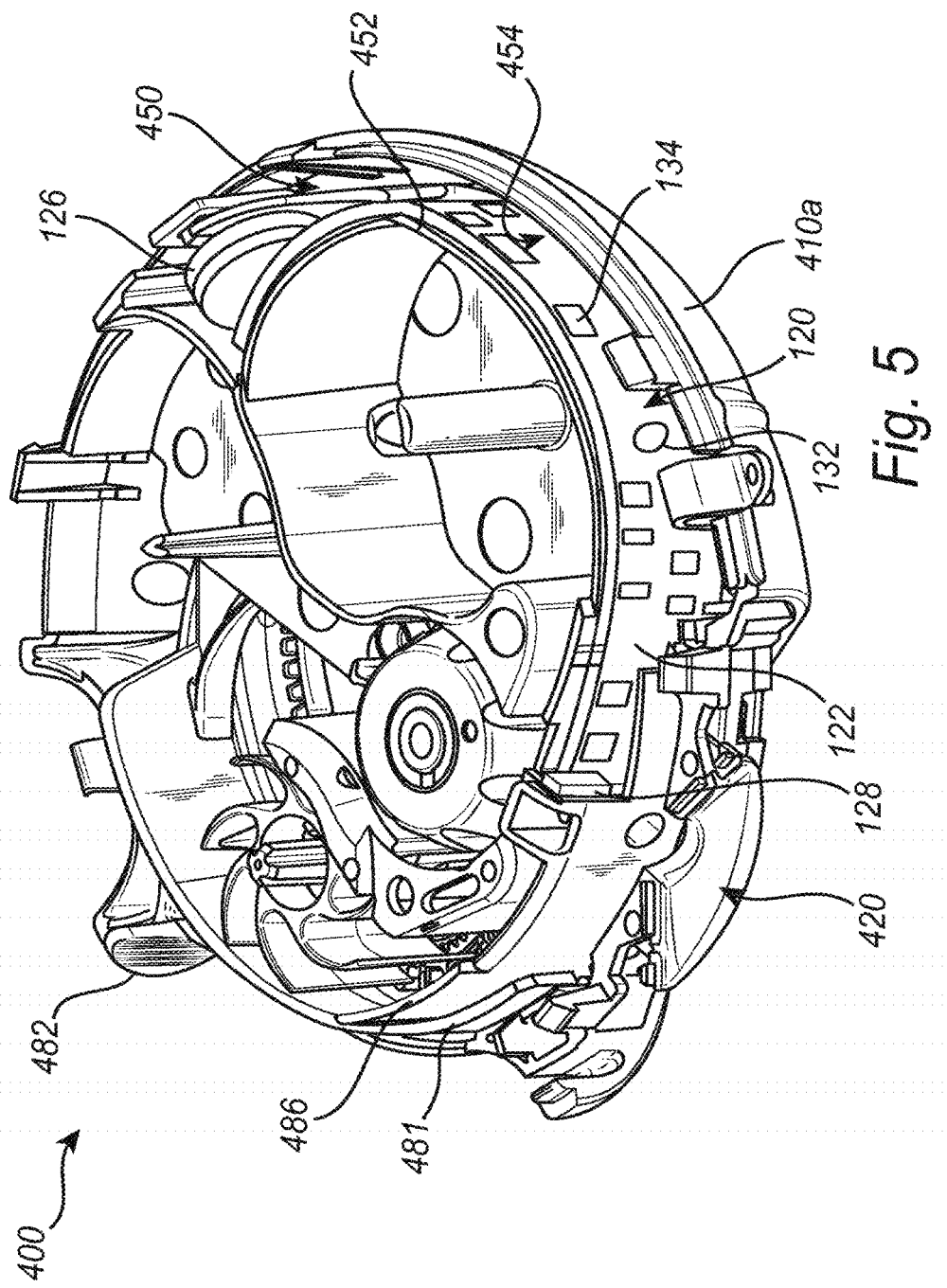
FIG. 5 is a cross-sectional interior perspective view of the inhalation device of FIG. 1A with an integrated electronics module.

FIG. 5 is a cross-sectional interior perspective view of the inhalation device 400 with an integrated electronics module 120, and without a flexible strip 401 installed inside. The electronics module 120 may be included in a cavity 450 that resides between an outer wall 452 surrounding the base winding wheel 470 and an inner wall 454 of the base 410a. Although placed in the cavity 450, it should be appreciated that the electronics module 120 may be integrated anywhere within the cavity of the inhalation device 400.

The electronics module 120 may include a printed circuit board (PCB) assembly 122, a switch (not shown), and a power supply (e.g., a battery 126). The PCB assembly 122 may include may include surface mounted components, such as a sensor system 128, a wireless communication circuit 134, the switch, and or one or more indicators, such as one or more light emitting diodes (LEDs) 132. Further, it should be noted that a portion of the manifold 486 has been removed from the inhalation device 400 of FIG. 5 so that the electronics module, and more specifically, the sensor system 128 could be more easily viewed. Although the portion of the manifold 486 is not illustrated in the inhalation device 400 of FIG. 5, the inhalation device 400 of FIG. 5 may in fact include the entire manifold 486 as illustrated in, for example, FIG. 2B. For example, the sensor system 128 may reside behind the portion of the manifold and be in fluid communication with the powder outlet 419.

The electronics module 120 may include a controller (e.g., a processor) and/or memory. The controller and/or memory may be physically distinct components of the PCB 122. Alternatively, the controller and memory may be part of another chipset mounted on the PCB 122, for example, the wireless communication circuit 134 may include the controller and/or memory for the electronics module 120. The controller of the electronics module 120 may include a microcontroller, a programmable logic device (PLD), a microprocessor, an application specific integrated circuit (ASIC), a field-programmable gate array (FPGA), or any suitable processing device or control circuit. The PCB 122 may be flexible, for example, such that it may reside within the cavity 450 of the inhalation device 400.

The controller may access information from, and store data in the memory. The memory may include any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The memory may be internal to the controller. The controller may also access data from, and store data in, memory that is not physically located within the electronics module 120, such as on a server or a smartphone.

The sensor system 128 may include one or more sensors, including, for example, one or more pressure sensors. The one or more pressure sensors may include a barometric pressure sensor (e.g., an atmospheric pressure sensor), a differential pressure sensor, an absolute pressure sensor, and/or the like. The sensors may employ microelectromechanical systems (MEMS) and/or nanoelectromechanical systems (NEMS) technology. The sensor system 128 may be configured to provide an instantaneous pressure reading to the controller of the electronics module 120 and/or aggregated pressure readings over time. The sensor system 128 may reside outside a flow pathway (e.g., from the mouthpiece 420, through the powder outlet 419, and across the manifold 486) the inhalation device 400. Alternatively, the sensor system 128 may reside within the flow pathway of the inhalation device 400.

As noted, in some examples, the sensor system 128 may include an atmospheric pressure sensor. Accordingly, the sensor system 128 may be configured to measure a plurality of atmospheric pressures within the inhalation device 400. It will be appreciated that the atmospheric pressure within the inhalation device 400 may be the same as or similar to the atmospheric pressure outside the inhalation device 400 when the inhalation device 400 is not being used. However, when a user inhales from the mouthpiece 420, the user's inhalation may cause the atmospheric pressure within the inhalation device 400 to decrease. Conversely, an exhalation into the mouthpiece 420 may cause the atmospheric pressure within the inhalation device 400 to increase. In both cases, the atmospheric pressure within the inhalation device 400 may differ from the atmospheric pressure outside of the inhalation device 400. Accordingly, certain parameters or metrics associated with the inhalation or exhalation may be determined by comparing changes in atmospheric pressure resulting from the inhalation or exhalation.

The switch may be activated by one or more components of the inhalation device 400. For example, the switch may be activated when the lever 424 is moved from the closed position to the open position, for example, to expose the powder outlet 419 and/or prepare a dose of medication. For example, the switch may be located on the PCB 122 and on an exterior surface of the manifold 486, such that the arcuate wall 481 of the lever 424 activates the switch when actuated by a user. For example, the switch may be compressed when the arcuate wall 481 is covering the powder outlet 419 (e.g., when the lever 424 is in the closed position), and become decompressed when the user presses on the finger tab 482 of the lever 424 to cause it to move (e.g., causes the lever 424 to pivot into the open position) to expose the powder outlet 419 and/or prepare a dose of medication. The decompression of the switch may actuate the switch. Although described with reference to an actuation of the lever 424, the switch may be actuated using other components of the inhalation device 400. For example, the switch may be actuated by movement of the mouthpiece cover 491, for example, such that the switch is not actuated when the mouthpiece cover 491 is closed and is actuated by means of opening the mouthpiece cover 491.

Figure 8:
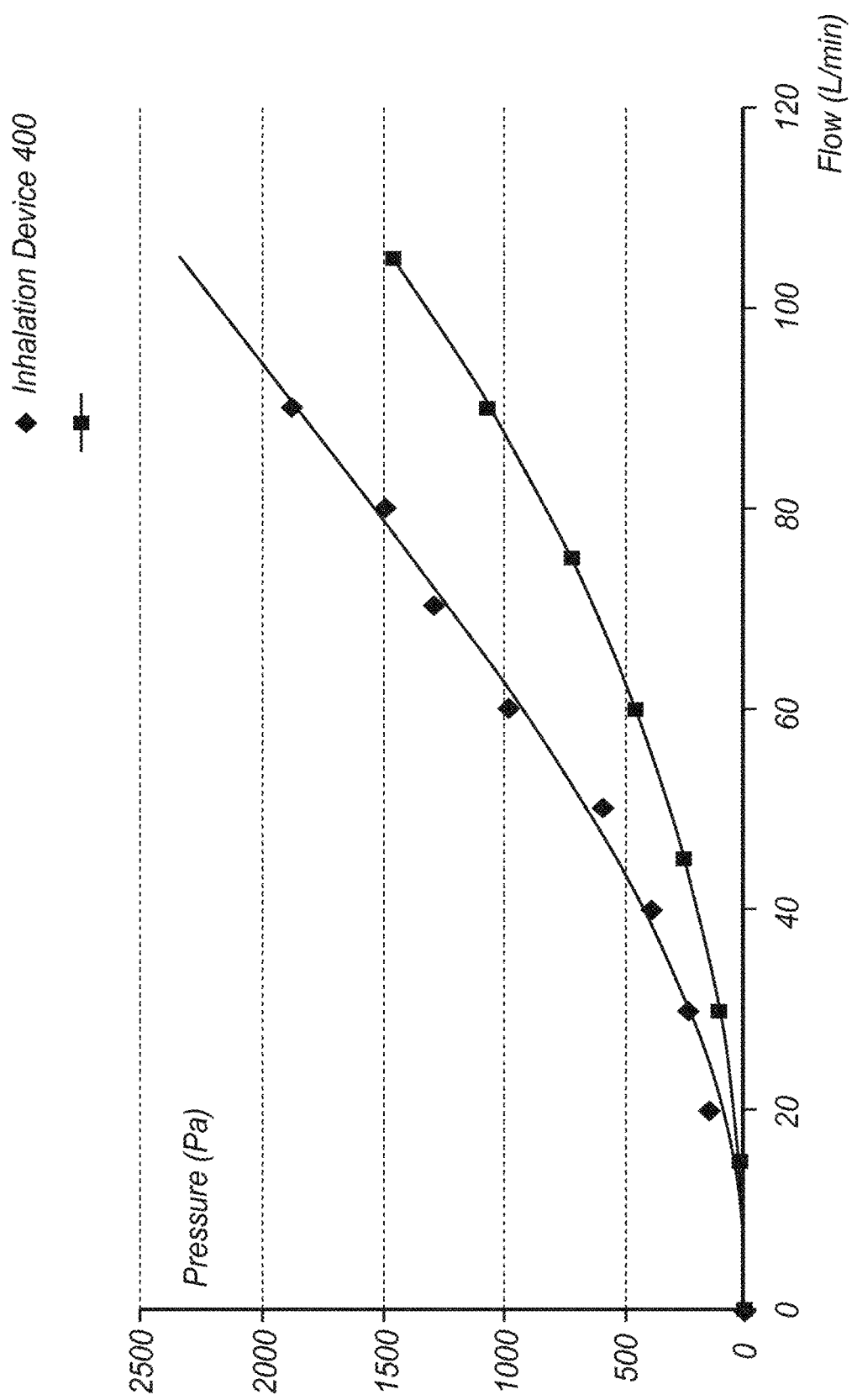
FIG. 8 is a diagram of an example pressure profile of the inhalation device of FIG. 1A.

The controller of the electronics module 120 may receive signals corresponding to pressure measurements from the sensor system 128. The controller may calculate or determine one or more inhalation parameters (e.g., a peak flow rate, a time to peak flow rate, an inhaled volume, an inhalation duration, etc.) using the signals received from the sensor system 128. The inhalation parameters (e.g., airflow metrics) may be indicative of a profile of airflow through the flow pathway of the inhalation device 400. For example, if the sensor system 128 records a change in pressure of 0.393 kilopascals (kPA), the electronics module 120 may determine that the change corresponds to an airflow rate of approximately 40 liters per minute (Lpm) through the flow pathway. Table 1 shows an example of airflow rates based on various pressure measurements. It will be appreciated that the airflow rates and profile shown in Table 1 are merely examples and that determined rates may depend on the size, shape, and design of the inhalation deice 400 and its components. Further, FIG. 8 is a diagram of an example pressure profile of the inhalation device of FIG. 1A.

TABLE 1

Examples of Average Air Flow Rate v. Average Pressure Drop near the Mouthpiece

| Flow Rate (Liters/min) | Average Pressure Drop (Pa) |
| --- | --- |
| 20 | 148 |
| 30 | 238 |
| 40 | 393 |
| 50 | 602 |
| 60 | 990 |
| 70 | 1300 |
| 80 | 1500 |
| 90 | 1880 |

As noted above, the controller of the electronics module 120 may receive signals corresponding to pressure measurements from the sensor system 128, and calculate or determine one or more inhalation parameters accordingly. The inhalation parameters may include one or more of an average flow of an inhalation/exhalation, a peak flow of an inhalation/exhalation (e.g., a maximum inhalation received), a volume of an inhalation/exhalation, a time to peak of an inhalation/exhalation, and/or the duration of an inhalation/exhalation. The inhalation parameters may also be indicative of the direction of flow through the flow pathway. That is, a negative change in pressure may correspond to an inhalation from the mouthpiece 420, while a positive change in pressure may correspond to an exhalation into the mouthpiece 420. When calculating the inhalation parameters, the electronics module 120 may be configured to eliminate or minimize any distortions caused by environmental conditions. For example, the electronics module 120 may "zero out" to account for changes in atmospheric pressure before or after calculating the inhalation parameters. The one or more pressure measurements and/or inhalation parameters may be timestamped and stored in the memory of the electronics module 120.

The controller of the electronics module 120 may compare signals received from the sensor system 128 and/or the determined inhalation parameters to one or more thresholds or ranges, for example, as part of an assessment of how the inhalation device 400 is being used and/or whether the use is likely to result in the delivery of a full dose of medication. For example, where the determined inhalation parameter corresponds to an inhalation with an airflow rate below a particular threshold, the electronics module 120 may determine that there has been no inhalation or an insufficient inhalation from the mouthpiece 420 of the inhalation device 400. If the determined inhalation parameter corresponds to an inhalation with an airflow rate above a particular threshold, the electronics module 120 may determine that there has been an excessive inhalation from the mouthpiece 420. If the determined inhalation parameter corresponds to an inhalation with an airflow rate within a particular range, the electronics module 120 may determine that the inhalation is "good," or likely to result in a full dose of medication being delivered. As noted above, the electronics module 120 may include indicators, such as an LED. The indicators may be configured to provide feedback to users regarding their use of the inhalation device 400. Thus, in one example, an LED 132 may illuminate or change color if the inhalation parameters correspond to a good inhalation or to no inhalation. The inhalation parameters may be computed and/or assessed via external devices as well (e.g., partially or entirely).

More specifically, the wireless communication circuit 134 of the electronics module 120 may include a transmitter and/or receiver (e.g., a transceiver), as well as additional circuitry. For example, the wireless communication circuit 134 may include a Bluetooth chip set (e.g., a Bluetooth Low Energy chip set), a ZigBee chipset, a Thread chipset, etc. As such, the electronics module 120 may wirelessly provide data such as pressure measurements, inhalation parameters and/or other conditions related to usage of the inhalation device 400, to an external device, including a smartphone. The external device may include software for processing the received information and for providing compliance and adherence feedback to users of the inhalation device 400 via a graphical user interface (GUI).

The battery 126 may provide power to the components of the PCB 122. The battery 126 may be any suitable source for powering the electronics module 120, such as a coin cell battery, for example. The battery 126 may be rechargeable or non-rechargeable. The battery 126 may be housed by a battery holder (not shown). The battery holder may be secured to the PCB 122, the inner wall 454 of the base 410a, and/or the like, such that the battery 126 maintains continuous contact with the PCB 122 and/or is in electrical connection with the components of the PCB 122. The battery 126 may have a particular battery capacity that may affect the life of the battery 126. As will be further discussed below, the distribution of power from the battery 126 to the one or more components of the PCB 122 may be managed to ensure the battery 126 can power the electronics module 120 over the useful life of the inhalation device 400 and/or the medication contained therein.

Although not illustrated, in one or more examples, the inhalation device 400 may include multiple flexible strips of medication. For instance, the inhalation device 400 may include two flexible strips of two different types of medication, and the lever 424 may be configured to advance both flexible strips of medication (e.g., simultaneously or successively). Further, the actuation of the lever 424 may advance both flexible strips of medication so that a base sheet and a lid sheet of each flexible strip are pulled apart to expose a previously unopened pocket from each of the flexible strips of medication. The released powder medication from the pockets of each of the flexible strips may be directed to a mixing chamber internal to the body of the inhalation device for inhalation by the patient through the mouthpiece 420. As such, the inhalation device 400 may provide different types of medications to be stored separately, but released and delivered to the patient as a combined medication.

Moreover, it should be appreciated that the inhalation device 400 may include any number of flexible strips of medication, and, for example, the inhalation device 400 may be configured such that pockets from any number of flexible strips of medication are opened in one or more stages (e.g., through the use of a single actuation, such as by way of a single actuation of the level 424). For example, the inhalation device 400 may be configured such that actuation (e.g., a single actuation) may advance a first and second strip of medication to open respective pockets of the first and second strips and combine the medication therein, and further advance one or more additional strips of medication to open respective pockets, and combine the medication from the additional strip(s) with the combined medication from the first and second strips. As such, the inhalation device 400 may be configured to combine any number of types of medication into a single dose, potentially in more than one stage, while keeping the individual types of medication stored in separate flexible strips.

Further, it should be appreciated that in some examples, the inhalation device 400 may provide for a single mechanism to perform any combination of exposing the mouthpiece 420 from under the mouthpiece cover 491, exposing the powder outlet 419, preparing a dose of medication (e.g., by advancing one or more flexible strips of medication), and/or actuating a switch of the electronics module 120 to activate (e.g., switch on/off) one or more components of the electronics module 120 (e.g., change the power state of the electronics module 120). For example, the mouthpiece cover 491 and/or the lever 424 may be such a mechanism. Accordingly, in some examples, the inhalation device 400 may be configured such that movement of the mouthpiece cover 491 from the closed to open position causes the mouthpiece 420 to be exposed, along with one or more of the powder outlet 419 being exposed, a dose of medication be prepared (e.g., causes one or more flexible strips of medication to be advanced), and/or the switch of the electronics module 120 to be actuated (e.g., to change the power state of the electronics module 120). In such examples, the inhalation device 400 may not include the lever 424, as the functionality of the lever 424 may be performed by the mouthpiece cover 491. Or, for example, the lever 424 may be part of the mouthpiece cover 491, such that the lever 424 moves when the mouthpiece cover 419 is moved to expose the mouthpiece 420. Further, it should be appreciated, that in some examples, any other component of the inhalation device 400 (e.g., the lever 424) may be configured to cause any combination of exposing the mouthpiece 420 from under the mouthpiece cover 491, exposing the powder outlet 419, preparing a dose of medication (e.g., by advancing one or more flexible strips of medication), and/or actuating the switch of the electronics module 120.

The electronics module 120 may have a plurality of power states, each with respective power consumption levels. For example, the electronics module 120 may be configured to operate in a system off state, a sleep state, and/or an active state. The system off state may be characterized by very little or no power consumption, while the sleep state may be characterized by greater power consumption than the off state, and the active state may be characterized by greater power consumption than the sleep state. While the electronics module 120 is in the active state, the electronics module may operate in one or more modes, such as a measurement mode, a data storage/data processing mode, an advertising mode, and/or a connected mode. It should be appreciated that the electronics module 120 may operate in multiple modes at one time (e.g., the modes may overlap). For example, as described in more detail below, the electronics modules 120 may operate in the measurement mode and the data storage/data processing mode at discrete times or simultaneously. That is, the electronics module 120 may be perform all of the measurements prior to processing/storing the data, or the electronics module 120 may perform data processing/storage while at the same time also performing additional measurements (e.g., the electronics modules 120 may switch between the measurement mode and the data storage/data processing mode before either is complete).

In the system off state, the electronics module 120 may consume the least amount of power in relation to its other power states (e.g., the sleep state and the active state). In particular, the electronics module 120 may use a minimal amount of power to monitor a certain pin (or pins) on the controller but other components, such as the sensor system 128, the wireless communication circuit 134 (e.g., the Bluetooth radio), and memory may be powered off. The pin on the controller may be in electrical connection with the switch such that actuation of the switch may result in a certain reference signal on the pin. The reference signal may trigger the controller to transition from the off state.

The off state may be the initial state of the electronics module 120 after the inhalation device 400 is assembled or manufactured. Thus, the electronics module 120 may be in the off state prior to the inhalation device 400 being delivered to the user and/or prior to the lever 424 being moved from the closed position to the open position (e.g., before the first use of the inhalation device 400 by the user), which for example, may expose the powder outlet 419 and/or prepare a dose of medication opened for a first time. In addition, once the lever 424 has been actuated for the first time, the electronics module 120 may not return to the off state thereafter. In some examples, the controller may start its internal clock (e.g., an internal counter) when the electronics module 120 first exits the off state, and any timestamp data generated by the electronics module 120 may be a relative time based on internal clock of the controller. Accordingly, the internal clock may act as a counter that starts when the electronics module 120 exits the off state. Alternatively or additionally, the controller may include an internal system clock that knows the actual time (e.g., 4:05 pm EST on Nov. 18, 2017) and the timestamp data may include the actual time. In such examples, the controller may use power in the off state to run its real-time clock oscillator and to update its system clock.

As noted above, while the electronics module 120 is the active state, the electronics module 120 may operate in one or more modes, such as a measurement mode, a data storage/data processing mode, an advertising mode, and/or a connected mode. In the sleep state, the switch and the controller may continue to receive power from the battery 126, and the controller may continue to run its oscillator and periodically update its system clock (e.g., continue to increment the internal counter that was started when the electronics module 120 first exited the off state). In some examples, the controller may periodically update the system clock every 250 µs.

Further, while in the sleep state, the controller may continue to receive power from the battery 126 to control one or more additional components of the electronics module 120. For example, during the advertising mode, the controller may periodically power on the communication circuit 134 to wirelessly "advertise" to an external device that data is stored on the inhalation device 400 and is available for wireless download. The communication circuit 134 may transmit advertising packets at any interval that is suitable for managing the power consumption of the electronics module 120 when in the sleep state (e.g., as compared to the interval at which packets may be sent during the active state). For example, advertising packets may be transmitted every 10 seconds when the electronics module 120 is operating in the sleep state. It will be appreciated that the electronics module 120 may spend more time in the sleep state than in any of the other power states. Thus, at a given advertising rate, the electronics module 120 may consume the most power in the sleep state over the life of the inhalation device 400.

In the measurement mode, the controller of the electronics module 120 may power on the sensor system 128. The controller may cause the sensor system 128 to take pressure measurement readings for a predetermined time period (e.g., up to 60 seconds), until the lever 424 is closed (e.g., to cover the powder outlet 419), and/or until no changes in pressure are detected. The controller may turn off one or more components of the electronics module 120 while the sensor system 128 is capturing pressure measurement readings to further conserve power. The sensor system 128 may sample the pressure at any suitable rate. For example, the sensor system 128 may have a sample rate of 100 Hz and thus a cycle time of 10 milliseconds. The sensor system 128 may generate a measurement complete interrupt after the measurement cycle is complete. The interrupt may "wake" the controller or cause it to turn on one or more components of the electronics module 120. For example, after or while the sensor system 128 is sampling pressure measurements, the controller may process and/or store the pressure measurement data and, if measurements are complete, power off the sensor system 128.

In the data storage/data processing mode, the controller may power on at least a portion of the memory within the electronics module 120. The controller may process the readings from the sensor system 128 to determine inhalation parameters and store the inhalation parameters in memory. The controller may also compare the readings and/or the inhalation parameters to one or more thresholds or ranges to assess how the inhalation device is being used (e.g., whether the pressure readings correspond to no inhalation, a "good" inhalation, to an exhalation, etc.). Depending on the results of the comparison, the controller may drive the indicators to provide feedback to the user of the inhalation device 400. As noted above, the electronics module 120 may operate in the measurement mode and the data storage/data processing mode simultaneously.

In the advertising mode, the controller may power on the communication circuit 134 (e.g., the Bluetooth radio) to advertise to an external device that data is available from the inhalation device 400 and is ready for wireless download. Advertising packets may be transmitted at any interval and for any duration that is suitable for managing the power consumption of the electronics module 120 when in the advertising mode. For example, the communication circuit 134 may transmit advertising packets every 100 milliseconds (ms) for 3 minutes. Further, it should be appreciated that the advertising rate may vary based on the particular conditions of the electronics module 120. For example, the advertising rate may be "fast" (e.g., packets are transmitted every 100 ms) after the measurements and data processing/storage has occurred, while the advertising rate may be "slow" (e.g., packets are transmitted every 10 seconds) when the electronics module 120 is transitioning from the sleep state in other situations (e.g., not right after measurement and data processing/storage has occurred).

In the connected mode, the communication circuit 134 and memory may be powered on and the electronics module 120 may be "paired" with an external device, such as a smartphone. The controller may retrieve data from the memory and wirelessly transmit the data to the external device. The controller may retrieve and transmit all of the data currently stored in the memory. The controller may also retrieve and transmit a portion of the data currently stored in the memory. For example, the controller may be able to determine which portions have already been transmitted to the external device and then transmit the portion(s) that have not been previously transmitted. Alternatively, the external device may request specific data from the controller, such as any data that has been collected by the electronics module 120 after a particular time or after the last transmission to the external device. The controller may retrieve the specific data, if any, from the memory and transmit the specific data to the external device.

The electronics module 120 may transition between power states and/or operational modes based on certain conditions or events, such as the position of the level 484, the position of the mouthpiece cover 491, and/or the elapse of predetermined time periods. For example, the mouthpiece cover 491 may be closed and the electronics module 120 may be in the off state or the sleep state. After the cover 491 is opened, the lever 424 may be actuated (e.g., moved from the closed position to an open position to expose the powder outlet 419 and prepare a dose of medication), which may actuate the switch. For example, and as noted above, the switch may be located on an exterior surface of the manifold 486 such that the arcuate wall 481 of the lever 424 activates the switch when actuated by a user. For example, the switch may compressed when the arcuate wall 481 is covering the powder outlet 419, and become decompressed when the user presses on the finger tab 482 of the lever 424 to cause it to move (e.g., causes the lever 424 to pivot) to expose the powder outlet 419 and/or prepare a dose of medication. The decompression of the switch may actuate the switch. Although described with reference to an actuation of the lever 424, the switch may be actuated using other components of the inhalation device 400. For example, the switch may be actuated by movement of the mouthpiece cover 491, for example, such that the switch is not actuated when the mouthpiece over is closed and is actuated by means of opening the mouthpiece cover 491. The actuation of the switch may cause the electronics module 120 to transition from one state (e.g., the system off state or sleep state) to another state (e.g., the active state). Further, as the actuation of the switch may cause the electronics module 120 to begin operating in one or more operational modes, such as the measurement mode and/or the data storage/data processing mode. For example, FIG. 6A-B illustrate an example flow diagram 200 that illustrates an example process for transitioning between one or more power states and/or operational modes associated with the inhalation device 400.

Figure 6A:
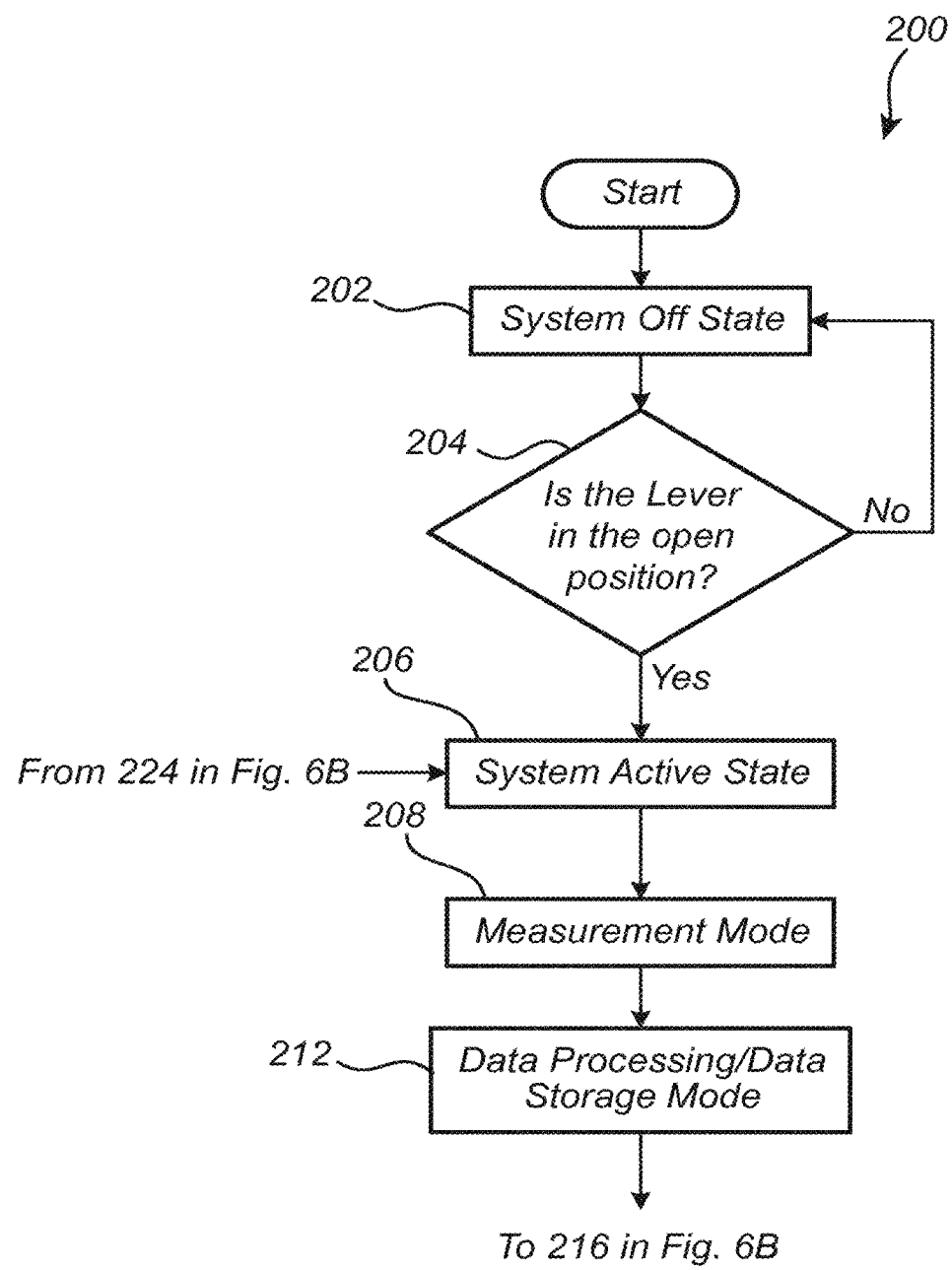
FIGS. 6A and 6B include a flow diagram that illustrates an example process for transitioning between one or more power states and/or operational modes associated with the inhalation device of FIG. 1A.
Figure 6B:
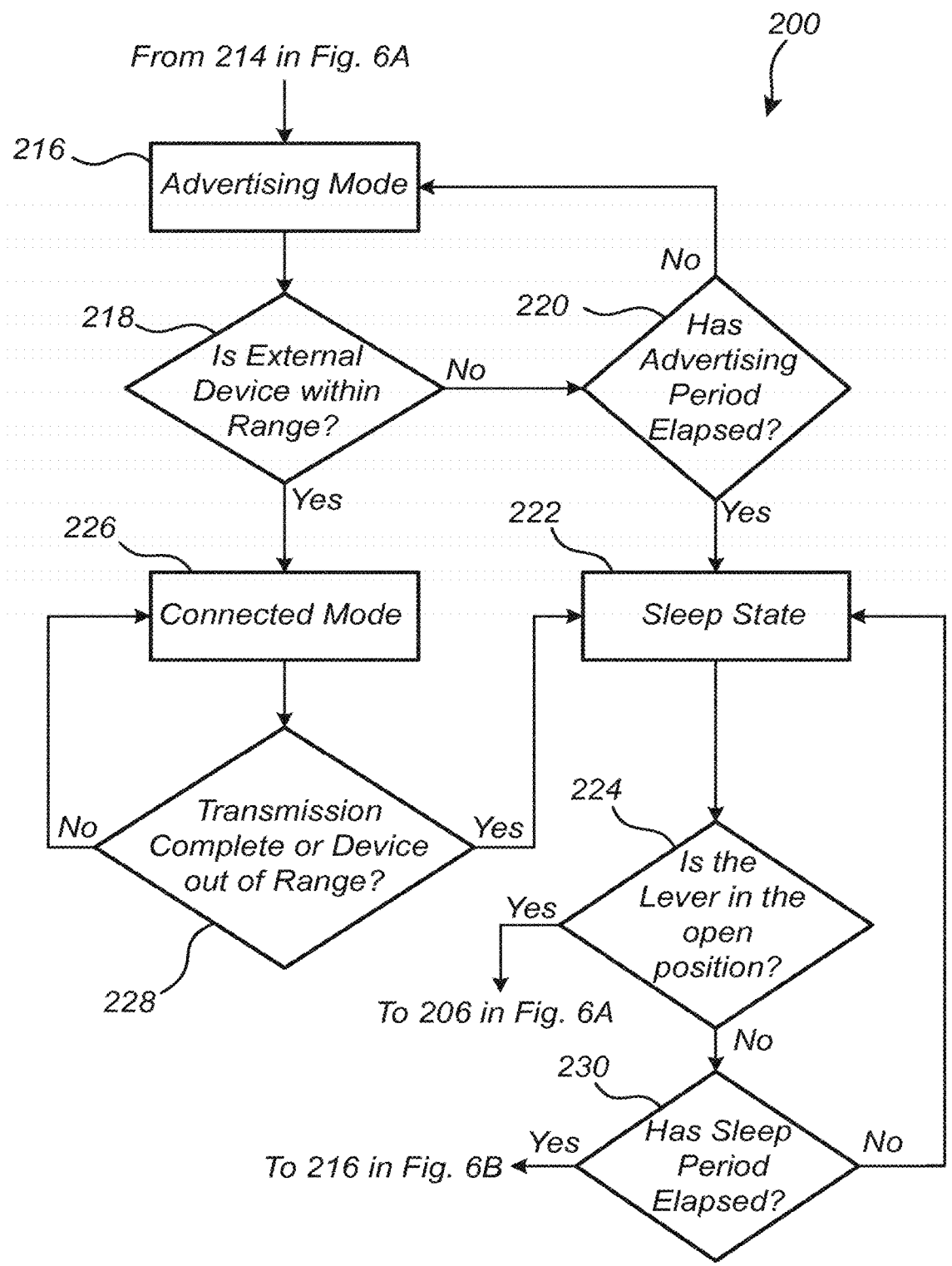

FIG. 6A-B illustrate an example procedure 200 for transitioning between one or more power states and/or operational modes associated with the inhalation device 400. Although described with reference to the inhalation device 400, any inhalation device may perform the procedure 200. The electronics module 120 of the inhalation device 400 may be in the off state at 202, when the procedure 200 begins. The mouthpiece cover 491 may be in the closed position and the user may not have actuated the lever 424 for the first time when the electronics module 120 is in the off state at 202. As noted herein, the off state may be characterized by little or no power consumption by the electronics module 120. At 204, the electronics module 120 may determine whether the lever 424 has been moved from a first, closed position to a second, open position (e.g., whether the lever 424 has been actuated). If the electronics module 102 determines that the lever 424 has not been moved into the open position, then the electronics module 120 may reside in the off state at 202.

If the electronics module 120 determines that the lever 424 has been moved into the open position at 204, then the electronics module 120 may enter the system active state at 206. The active state may be characterized by greater power consumption than the off state (e.g. and the sleep state). When in the active state, the electronics module 120 may operate in one or more modes, such as a measurement mode, a data storage/data processing mode, an advertising mode, and/or a connected mode. For example, the actuation of the lever 424 may cause the switch to be actuated. The actuation of the switch may cause the electronics module 120 to transition from the off state to the active state. Further, the actuation of the lever 424 may advance the flexible strip 401 and prepare a dose of medication for a use to inhale.

While in the active state, and after the lever 424 has been actuated, the electronics module 120 may enter a measurement mode at 208. During the measurement mode, the electronics module 120 may power on the sensor system 128 and may cause the sensor system 128 to take pressure measurement readings for a predetermined time period (e.g., up to 60 seconds) and/or until the mouthpiece cover 491 is closed or no changes in pressure are detected.

In some examples, the electronics module 120 may remain in the measurement mode until the pressure measurement cycle is complete. The pressure measurement cycle may persist for a predetermined period of time and/or until a particular event is detected. For example, the pressure measurement cycle may persist for up to 60 seconds, even if the mouthpiece cover 491 has been closed and/or the lever 424 has disengaged from the switch. Alternatively, the pressure measurement cycle may persist for up to 60 seconds or until the mouthpiece cover 491 has been closed or until no changes in pressure are detected for 10 seconds, whichever comes first. It will be appreciated that the foregoing conditions are merely examples and that any suitable criteria can be used.

At 212, the electronics module 120 may enter the data processing/data storage mode. During the data processing/data storage mode, the electronics module 120 may power on at least a portion of the memory within the electronics module 120. The electronics module 120 may process the readings from the sensor system 128 to determine inhalation parameters/metrics and store the inhalation parameters/metrics in memory. The electronics module 120 may also compare the readings and/or the inhalation parameters/metrics to one or more thresholds or ranges to assess how the inhalation device is being used (e.g., whether the pressure readings correspond to no inhalation, a "good" inhalation, to an exhalation, etc.). Depending on the results of the comparison, the electronics module 120 may drive the indicators to provide feedback to the user of the inhalation device 400.

Although not illustrated by the procedure 200, the electronics module 120 may operate in the measurement mode and the data storage/data processing mode simultaneously. For example, the electronics module 120 may switch (e.g., periodically switch) between the measurement mode and the data processing/data storage mode. For example, after or while the electronics module 120 is receiving pressure measurements, the electronics module 120 may process and/or store the pressure measurement data.

The electronics module 120 may remain in the data storage/data processing mode for a predetermined period of time to process and store the pressure measurement readings from the sensor system 128. For example, the electronics module 120 may remain in the data storage/data processing mode for up to 60 ms. The electronics module 120 may, for example, use up to 50 ms to process and compute inhalation parameters from the pressure measurement readings and up to 10 ms to store the pressure measurements and/or inhalation parameters in the memory. Alternatively, the electronics module 120 may remain in the data storage/data processing mode for whatever duration it takes for the controller to process and store the pressure measurement readings and/or air flow metrics.

The electronics module 120 may enter the advertising mode at 216. For example, the electronics module 120 may enter the advertising mode after the predetermined period of time for data processing and data storage has elapsed, or after the controller has determined that such processing and storing are complete. During the advertising mode, the electronics module 120 may power on the communication circuit 134 (e.g., the Bluetooth radio) to advertise to an external device that data is available from the inhalation device 400 and is ready for wireless download. Advertising packets may be transmitted at any interval and for any duration that is suitable for managing the power consumption of the electronics module 120 when in the advertising mode. For example, the communication circuit 134 may transmit advertising packets every 100 milliseconds (ms) for 3 minutes. Further, it should be appreciated that the advertising rate may vary based on the particular conditions of the electronics module 120. For example, the advertising rate may be "fast" (e.g., packets are transmitted every 100 ms) after the measurements and data processing/storage has occurred (e.g., when transitioning from 212 to 216), whereas the advertising rate may be "slow" (e.g., packets are transmitted every 10 seconds) when the electronics module 120 is transitioning from the sleep state and without the lever 424 being moved to the open position (e.g., when transitioning from 230 to 216).

At 218, the electronics module 120 may determine if an external device is within range. If the external device does not come within a particular range of the electronics module 120 during the advertising mode, the electronics module 120 may determine whether an advertising period (e.g., 3 minutes) has elapsed at 220. The advertising period may be a period of time that the electronics module 120 continues to advertise to an external device before changing power states. If the advertising period has not elapsed, then the electronics module 120 may continue to advertise to the external device at 216. However, if the advertising period has elapsed, then the electronics module 120 may move to a sleep state at 222. The sleep state may be characterized by greater power consumption than the off state, but less power consumption than the on state.

The electronics module 120 may remain in the sleep state for a predetermined amount of time or until the electronics module determines that the lever 424 has been moved from the closed to the open position. For example, the electronics module 120 may periodically switch between the sleep state and the advertising mode (e.g., the slow advertising mode) of the active state. For example, at 224, the electronics module 120 may determine whether the lever 424 has been moved from the closed to the open position. If the lever 424 has been moved into the open position, then the electronics module 120 may enter the active state at 206. For example, the actuation of the lever 424 may cause the switch to be actuated. The actuation of the switch may cause the electronics module 120 to transition from the sleep state to the active state.

If the electronics module 120 determines that the lever 424 remains in the closed position, then the electronics module 120 may determine whether a sleep period (e.g., 10 seconds) has elapsed at 230. If the sleep period has not elapsed at 230, then the electronics module 120 may stay in the sleep state and return to 222. However, if the sleep period has elapsed at 230, then the electronics module 120 may return to the advertising mode of the active state at 216. When the electronics module 120 transitions from 230 to 216, the electronics module 120 may advertises at a different, possibly slower rate as compared to when the electronics module 120 transitions from 212 to 216 (e.g., such as once every 10 seconds as opposed to once every 100 ms). As such, the electronics module 120 may use less battery power during such advertising modes. Further, the electronics module 120 may periodically switch between the active state and the sleep state based on the advertising period and the sleep period (e.g., and while the mouthpiece cover 491 is in the closed position).

Returning to 218, if the external device (e.g., smartphone or tablet) comes within a particular range of the electronics module 120 during the advertising mode, the electronics module 120 may "pair" with the external device and enter the connected mode at 226. In the connected mode, the electronics module 120 may power on the communication circuit 134 and memory. The electronics module 120 may retrieve data from the memory and wirelessly transmit the data to the external device. At 228, the electronics module 120 may determine whether the transmission is complete or the external device is out of communication range. If the transmission is not complete and the external device is within the communication range, then the electronics module 120 will remain in the connected mode. However, if the transmission is complete or if the external device is out of the communication range, then the electronics module 120 will transition to the sleep state at 222.

During the connected mode, the electronics module 120 may retrieve and transmit all of the data currently stored in the memory, or the controller may retrieve and transmit a portion of the data currently stored in the memory. For example, the controller may be able to determine which portions have already been transmitted to the external device and then transmit the portion(s) that have not been previously transmitted (e.g., based on the internal counter). Alternatively or additionally, the external device may request specific data from the electronics module 120, such as any data that has been collected by the electronics module 120 after a particular time or after the last transmission to the external device. The electronics module 120 may retrieve the specific data, if any, from the memory and transmit the specific data to the external device.

Further, when connected with the external device, the electronics module 120 may be configured to transmit Bluetooth special interest group (SIG) characteristics for managing access to records stored in the module 120. The Bluetooth SIG characteristics may include one or more of a manufacturer name of the inhalation device 400, a serial number of the inhalation device 400, a hardware revision number of the inhalation device 400, and/or a software revision number of the inhalation device 400. When connected with the external device, the electronics module 120 may retrieve data from memory and transmit the data to the external device.

The inhalation device 400 may include a Quick Response (QR) code. The external device may include a camera and software application for accessing the camera and reading the QR code. The QR code may include a BLE passkey that is unique to the inhalation device 400. Upon reading or scanning the QR code using the camera, the software application may receive the BLE passkey associated with the device 400 and complete an authentication process, thereby enabling it to communicate with the electronics module 120 using the BLE passkey. If the communications session is subsequently lost because, for example, the inhalation device 400 moves out of range, the external device may be configured to use the BLE passkey to automatically pair with the electronics module 120 without using the QR code when the inhalation device 400 is back within range.

The inhalation device 400 may transmit an inhalation event, an inhalation parameter, a pressure measurement, a mouthpiece cover 491 opening or closing event, a lever 424 actuation event, an error event, an operating characteristic of the inhalation device (e.g., remaining battery life), and/or associated timestamps (e.g., based on the internal counter) to the external device when in the connected mode. For example, the signals generated by the switch, the pressure measurement readings taken by the sensory system 128, and/or the inhalation parameters computed by the controller of the electronics modules 120 may be timestamped and stored in memory. The foregoing data may be indicative of various usage parameters associated with the inhalation device 400. For example, as movement of the arcuate wall 481 of the lever 424 causes the switch to transition between "on" and "off," the controller of the electronics module 120 may use the signals from the switch to record and timestamp each transition. Further, as the transition of the switch between "on" and "off" may correlate to the position of lever 424 (e.g., closed and covering the powder outlet 419 or open/actuated to uncover the powder outlet 419 and/or prepare a blister of medication for delivery to the user), the electronics module 120 may be able to detect and track the position of the lever 424 over time. It will be appreciated that the electronics module 120 may be able to sense and track the status of the lever 424 without interfering with the delivery of medication through the flow pathway of the inhalation device 400.

The pressure measurement readings and/or the computed inhalation parameters may be indicative of the quality or strength of inhalation from the inhalation device 400. For example, when compared to a particular threshold or range of values, the readings and/or metrics may be used to categorize the inhalation as a certain type of event, such as a good inhalation event, a low inhalation event, a no inhalation event, or an excessive inhalation event.

The no inhalation event may be associated with pressure measurement readings and/or inhalation parameters below a particular threshold, such as an airflow rate less than 30 Lpm. The no inhalation event may occur when a user does not inhale from the mouthpiece 420 after opening the mouthpiece cover 491 and during the measurement cycle. The no inhalation event may also occur when the user's inspiratory effort is insufficient to ensure proper delivery of the medication via the flow pathway, such as when the inspiratory effort generates insufficient airflow to aerosolize the medication.

The low inhalation event may be associated with pressure measurement readings and/or inhalation parameters within a particular range, such as an airflow rate between 30 Lpm and 45 Lpm. The low inhalation event may occur when the user inhales from the mouthpiece 420 after opening the mouthpiece cover 491 and the user's inspiratory effort causes at least a partial dose of the medication to be delivered via the flow pathway. That is, the inhalation may be sufficient to cause a portion of the medication is aerosolized.

The good inhalation event may be associated with pressure measurement readings and/or inhalation parameters above the low inhalation event, such as an airflow rate between 45 Lpm and 200 Lpm. The good inhalation event may occur when the user inhales from the mouthpiece 420 after opening the mouthpiece cover 491 and the user's inspiratory effort is sufficient to ensure proper delivery of the medication via the flow pathway, such as when the inspiratory effort generates sufficient airflow to aerosolize a full dose of medication.

The excessive inhalation event may be associated with pressure measurement readings and/or inhalation parameters above the good inhalation event, such as an airflow rate above 200 Lpm. The excessive inhalation event may occur when the user's inspiratory effort exceeds the normal operational parameters of the inhalation device 400. The excessive inhalation event may also occur if the device 400 is not properly positioned or held during use, even if the user's inspiratory effort is within a normal range. For example, the computed airflow rate may exceed 200 Lpm if the air vent is blocked or obstructed (e.g., by a finger or thumb) while the user is inhaling from the mouthpiece 420.

It will be appreciated that any suitable thresholds or ranges may be used to categorize a particular event. It will further be appreciated that some or all of the events may be used. For example, the no inhalation event may be associated with an airflow rate below 45 Lpm and the good inhalation event may be associated with an airflow rate between 45 Lpm and 200 Lpm. As such, the low inhalation event may not be used at all in some cases.

The pressure measurement readings and/or the computed inhalation parameters may also be indicative of the direction of flow through the flow pathway of the inhalation device 400. For example, if the pressure measurement readings reflect a negative change in pressure, the readings may be indicative of air flowing out of the mouthpiece 420 via the flow pathway. If the pressure measurement readings reflect a positive change in pressure, the readings may be indicative of air flowing into the mouthpiece 420 via the flow pathway. Accordingly, the pressure measurement readings and/or inhalation parameters may be used to determine whether a user is exhaling into the mouthpiece 420, which may signal that the user is not using the device 400 properly.

By timestamping and storing the signals generated by the switch, the pressure measurement readings taken by the sensory system 128, and/or the inhalation parameters computed by the controller of the electronics module 120, the data collected and stored by the electronics module 120 may be used to determine whether the usage parameters are suitable or appropriate over a given period of time. As such, the data may be indicative of other events, such as an overuse event, an underuse event, or an optimal use event.

For example, the user of the inhalation device 400 may be prescribed by his or her doctor to take two doses of medication via the inhalation device 400 each day. In addition, the medication contained in the inhalation device 400 may also be approved (e.g., for safety and regulatory purposes) to be taken no more eight times each day. The overuse event may occur if the electronics module 120 records more than two good inhalations in a twenty-four hour period (i.e., the actual dosing is exceeding the prescribed number of doses) and/or if the electronics module 120 records more than eight good inhalations in a twenty-four hour period (i.e., the actual dosing is exceeding the regulatory approved number of doses). The underuse event may occur if the electronics module 120 records less than two good inhalations in a twenty-four hour period (i.e., the actual dosing is below the prescribed number of doses). The optimal use event may occur if the electronics module 120 records two good inhalations in a twenty-four hour period (i.e., the actual dosing is below the prescribed number of doses). It will be appreciated that optimal use events may be indicative of a user who is adherent. It will further be appreciated that the prescribed dosing schedule and/or the maximum approved dosing schedule may depend on the type of medication contained in the inhalation device 400. In addition, the events may be defined using any suitable number of doses over any suitable period of time, such as two doses per day, fourteen doses per week, 60 doses per month, etc.

The data collected and stored by the electronics module 120 may also be used to estimate the number doses that have been delivered from the inhalation device 400 and/or estimate the number of doses that remain in the flexible strip 401. For example, each time the switch is activated via the actuation of the lever 424, the signal generated by the switch may be counted as a dose delivery event. Thus, the inhalation device 400 may be deemed to have delivered 60 doses when the lever 424 is actuated 60 times. The inhalation device 400 may be configured to store enough medication in the flexible strip 401 to deliver a predefined total number of doses, such as a total of 200 doses. As such, the inhalation device 400 may also be deemed to have 140 doses remaining after the lever 424 is actuated 60 times.

As noted above, medication will not be delivered from the flexible strip 401 upon the user actuating the lever 424 if a previous dose of medication was not properly administered. Thus, it will be appreciated that counting the number of doses based on the actuation of the lever 424 may not accurately reflect the actual number of doses delivered by the device 400 if, for example, a user actuates the lever 424 without inhaling from the mouthpiece 420. Accordingly, other data in the electronics module 120 may be used and/or combined with the signals from the switch to determine the number of doses delivered and/or remaining in the inhalation device 400. For example, a dose may be counted as delivered each time a computed inhalation parameters is above a threshold or within a particular range, such as when a good inhalation event has been recorded. By calculating and tracking the number of doses delivered and/or remaining, the electronics module 120 may be configured to identify a refill event, which may be indicative of a time when a user should consider obtaining a new inhalation device 400.

The data collected and stored by the electronics module 120 may also be used to determine various error conditions associated with the operation of the module 120. For example, when processing the data the electronics module 120 may generate a bad data flag, a data corrupt flag, a timestamp error flag, and/or the like. The electronics module 120 may generate the bad data flag when the controller of the electronics module 120 determines that one or more signals received from the sensor system 128 are outside a predetermined range, which may indicate a malfunction in the sensor system 128. The electronics module 120 may generate the data corrupt flag when the controller's cyclic redundancy check (CRC) of data does not match what is stored in memory, which may indicate a malfunction of the memory and/or that the data in the memory has been corrupted. The electronics module 120 may generate a timestamp error flag when the controller loses its electrical connection with the battery 126, causing the controller's system clock to reset. If the controller's system clock is reset, the controller may restart its clock from the last stored counter value.

The electronics module 120 (e.g., and/or a mobile application residing on an external device) may also analyze the recorded events over a period of time to identity multiple error events, which may include a pattern of use indicative of a user who is not familiar with the proper operation of the inhalation device 400 and thus a user who may require further training. For example, the electronics module 120 may look at the number of good inhalation events over a predetermined period of time and/or over a predetermined number of actuations of the lever 424. A multiple error event may occur when a user has had only two good inhalation events over the past week, or has had six or less good inhalations over the last twelve actuations of the lever 424. It will be appreciated that the foregoing conditions are merely examples and that any suitable pattern of use may be used to define a multiple error event.

The data collected and stored by the electronics module 120 may also be used to assess the amount of power remaining in the battery 126. For example, the controller may determine whether there is a low battery event or condition, such as whether the battery has less than a predetermined amount of charge remaining (e.g., below 10%).

It will be appreciated that electronics module 120 may process and analyze the data stored in memory (e.g., the signals generated by the switch, the pressure measurement readings taken by the sensory system 128 and/or the inhalation parameters computed by the controller of the electronics module 120) to determine the usage parameters associated with the inhalation device 400. For example, the electronics module 120 may process the data to identify no inhalation events, low inhalations events, good inhalation events, excessive inhalation events, and/or exhalation events. The electronics module 120 may also process the data to identify underuse events, overuse events, and optimal use events. The electronics module 120 may further process the data to estimate the number of doses delivered and/or remaining and to identify error conditions, such as those associated with a timestamp error flag. The electronics module 120 may inform the user of some or all of the foregoing usage parameters of the inhalation device 400 using the indicators, such as one or more LEDs. As an example, the electronics module 120 may illuminate an LED 132 to indicate a good inhalation event or change the color of an LED 132 to indicate a low inhalation event or a no inhalation event. The usage parameters may be indicated to the user via any combination of light sequences and/or light color schemes.

It will further be appreciated that the data stored in the memory of the electronics module 120 (e.g., the signals generated by the switch, the pressure measurement readings taken by the sensory system 128 and/or the inhalation parameters computed by the controller of the electronics module 120) may also be transmitted to an external device, which may process and analyze the data to determine the usage parameters associated with the inhalation device 400. Further, a mobile application residing on the mobile device may generate feedback for the user based on data received from the electronics module 120. For example, the mobile application may generate daily, weekly, or monthly report, provide confirmation of error events or notifications, provide instructive feedback to the user, and/or the like.

FIG. 7 is a diagram of an example system 300 including the inhalation device 400, an external device (e.g., a mobile device 304), a public and/or private network 306 (e.g., the Internet, a cloud network), a health care provider 308, and a third party 310 (e.g., friends, family, pharmaceutical manufacturer, etc.). The mobile device 304 may include a smart phone (e.g., an iPhone® smart phone, an Android® smart phone, or a Blackberry® smart phone), a personal computer, a laptop, a wireless-capable media device (e.g., MP3 player, gaming device, television, a media streaming devices (e.g., the Amazon Fire TV, Nexus Player, etc.), etc.), a tablet device (e.g., an iPad® hand-held computing device), a Wi-Fi or wireless-communication-capable television, or any other suitable Internet-Protocol-enabled device. For example, the mobile device 304 may be configured to transmit and/or receive RF signals via a Wi-Fi communication link, a Wi-MAX communications link, a Bluetooth® or Bluetooth Smart communications link, a near field communication (NFC) link, a cellular communications link, a television white space (TVWS) communication link, or any combination thereof. The mobile device 304 may transfer data through the public and/or private network 306 to the health care provider 308 and/or one or more third parties 310 (e.g., friends, family, pharmaceutical company, etc.).

As noted herein, the inhalation device 400 may include a communication circuit 134, such as a Bluetooth radio, for transferring data to the mobile device 304. The data may include the signals generated by the switch, the pressure measurement readings taken by the sensory system 128 and/or the inhalation parameters computed by the controller of the electronics module 120. The inhalation device 400 may receive data from the mobile device 304, such as, for example, program instructions, operating system changes, dosage information, alerts or notifications, acknowledgments, etc.

The mobile device 304 may process and analyze the data to determine the usage parameters associated with the inhalation device 400. For example, the mobile device 304 may process the data to identify no inhalation events, low inhalations events, good inhalation events, excessive inhalation events and/or exhalation events. The mobile device 304 may also process the data to identify underuse events, overuse events and optimal use events. The mobile device 304 may further process the data to estimate the number of doses delivered and/or remaining and to identify error conditions, such as those associated with a timestamp error flag. The mobile device 304 may include a display and software for visually presenting the usage parameters through a GUI on the display.

Figure 9:
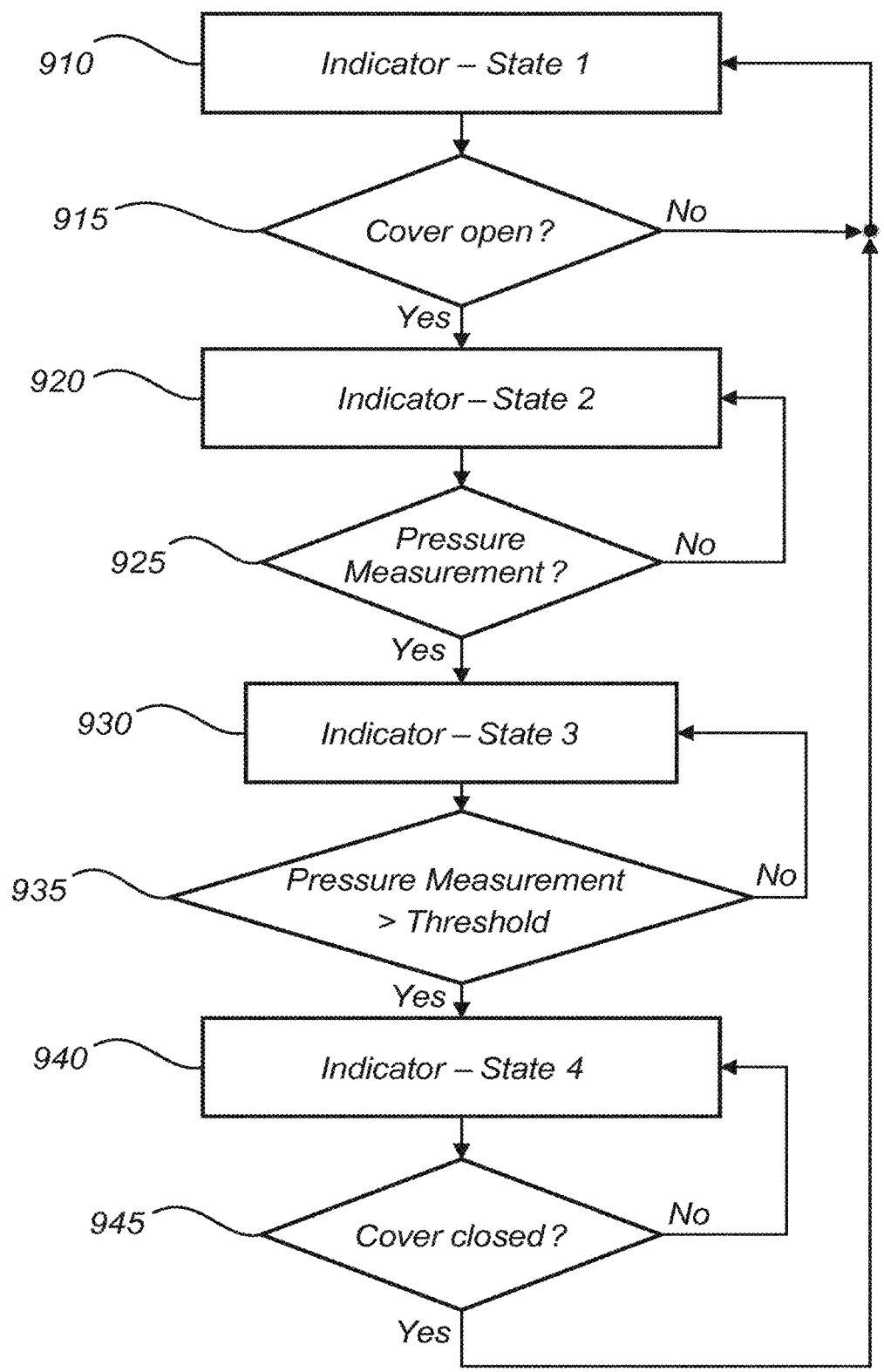
FIG. 9 is an example flow diagram of various states of an indicator of the inhalation device of FIG. 1A.

As noted herein, the inhalation device 400 may include one or more indicators, such as light-emitting diodes (LEDs) 132. The LED 132 may have multiple colors and/or multiple modes of indication. For example, the LED 132 may be on, off, flashing, and/or illuminate in multiple colors. The LED 132 may use different patterns of flashing. FIG. 9 is an example flow diagram of various states of the inhalation device 400 with a single indicator (e.g., LED 132). At 910, the lever 424 of the inhalation device 400 may be closed and the LED 132 is in state 1. For example, the LED 132 may be off in state 1. When the inhalation device 400 (e.g., through the switch of the e-module 120 ) detects that the lever 424 has been actuated at 915, the LED 132 may be in (e.g., changed to) state 2 at 920. For example, the LED 132 may illuminate or flash in state 2. When the inhalation device 400 detects a pressure measurement (e.g., at a first threshold) via the pressure sensor, the LED 132 may be in state 3 at 930. For example, the LED 132 may illuminate or flash in state 3. The pressure measurement may be indicative of (e.g., caused by) the user inhaling medication.

When the inhalation device 400 detects that the pressure measurement exceeds a predetermined amount at 935 (e.g., which may be indicative of a full dose of medication being administered to the user), the LED 132 may be in state 4 at 940. For example, the LED 132 may illuminate in state 4. If the inhalation device 400 detects that the lever 424 returns to the closed position (e.g., the cover 491 is closed) at 945, then the LED 132 may be in state 1 at 910. For example, the LED 132 may be off in state 1. In one or more embodiments, 925 and 930 may be omitted such that the inhalation device 400 may proceed to 935 from 920.

The LED 132 may be on, off, flash, and/or illuminate in different colors to indicate different states. For example, LED 132 may indicate state 2 with green and state 4 with blue. Further, the example state diagrams may include the states 1, 2, 3, and 4 of the LED 132 being in any combination of an off state, an on state, and/or a flashing state. Moreover, if the LED 132 is a light, the on state and/or flashing state may be characterized by the light being illuminated in one or more of a plurality of colors. The indicator may use different patterns of flashing. For example, example state diagrams are provided in Table 2 below:

TABLE 2

Example configurations of the LED

| Example State Diagrams | State 1 | State 2 | State 3 | State 4 |
|---|---|---|---|---|
| Ex. 1 | Off | Flash | Flash | On |
| Ex. 2 | Off | On | On | Off |
| Ex. 3 | Off | On - Color 1 | On - Color 1 | On - Color 2 |
| Ex. 4 | Off | On - Color 1 | Flash | On - Color 2 |
| Ex. 5 | Off | Off | Off | On |
| Ex. 6 | Off | On - Color 1 | On - Color 2 | On - Color 3 |

In example 1, the LED is off in state A1 (e.g., when the lever 424 is closed), flashing in state 2 (e.g., to indicate that a dose is ready), flashing in state 3 (e.g., while the user is inhaling), and on in state 4 (e.g., when the dose has been administered). In example 2, the LED 132 is off in state 1, and on in states 2, 3, and off in state 4. In example 3, the LED 132 is off in state 1, on in a first color in states 2 and 3, and on in a second color in state 4. In example 4, the LED 132 is off in state A1, on in a first color in state 2, flashing in state 3, and on in a second color in state 4. In example 5, the LED 132 is off in states 1, 2, and 3, and on in state 4. In example 6, the LED 132 is off in state 1, on in a first color in state 2, on in a second color in state 3, and on in a third color in state 4. There may be other methods of indicating the states. For example, the indicators may include multi-light and/or multi-color configurations. Further, the inhalation device 400 may include one or more visual indicators that progress through any combination of states, where each state is defined by one or more of the visual indicators being on, off, flashing, and/or illuminated in one or a combination of different colors.

Table 3 provides additional examples of the states of the LED 132 of the inhalation device 400. The examples 7-9 may include any number or combination of the states provided herein.

TABLE 3

Example configurations of the LED

| States | Example 7 | Example 8 | Example 9 |
|---|---|---|---|
| Confirm when dose is prepared and ready to inhale via LED 132 | ON | ON | Slow Flashing |
| Confirm good inhalation effort via LED 132 | OFF | Slow Flashing | ON |
| Cover 491 closed or 1 Minute Timeout | OFF | OFF | OFF |
| Error notifications via LED 132 | | | |
| No inhalation detected | Stays ON | Stays ON | Stays Slow Flashing |
| Exhaled into Inhalation device 400 prior to inhalation | Fast Flashing | OFF | OFF |
| Left cover 491 open >1 minute | OFF | OFF | OFF |

The inhalation device 400 may determine that the flexible strip 401 is empty, for example, via a dose counter. The dose counter may be mechanical and/or electrical. For example, the electronics module of the inhalation device 400 may determine that the flexible strip 401 is empty. When the inhalation device 400 determines that the flexible strip 401 is empty and when the lever 424 is subsequently actuated, the inhalation device 400 may leave the LED(s) 132 in the off state. This, for example, may indicate to the user that the inhalation device 400 is not ready for inhalation because the inhalation device 400 is out of medication. The inhalation device 400 may indicate that the flexible strip 401 is empty using one or more of the indication techniques described herein (e.g., sold light, colored light, flashing light, one or more indicators, etc.).

Although not illustrated, the inhalation device 400 may include one or more additional indications, such as a plurality of LEDs. For example, the inhalation device 400 may further provide a dose reminder indication to the user. The dose reminder indication may indicate that it is time for the user to take a dose of medication. For example, the inhalation device 400 may use one or more indicators (e.g., lights, sounds, haptic feedback, etc.) to provide a dose reminder to the user.

Although described primarily with reference to visual indicators (e.g., one or more LEDs and/or light states), one or more of the embodiments/examples described herein may comprise other indicators. For example, the indicators may comprise visual indicators (e.g., one or more lights and/or light states), audible indicators (e.g., one or more buzzers/speakers and/or sounds), and/or haptic feedback indicators (e.g., one or more haptic feedback devices and/or haptic feedback states/operations).

What is claimed is:

1. An electronics module for an inhaler, the electronics module comprising:
a power supply, a wireless communication circuit, a switch, a sensor, and a processor, wherein the processor is configured to:
cause the electronics module to transition from a sleep state to an active state in response to actuation of the switch, wherein the electronics module is configured to provide power to the wireless communication circuit and the switch when in the sleep state, and wherein the electronics module is configured to provide power to the sensor, the processor and the wireless communication circuit when in the active state;
generate a lever actuation event in response to actuation of a lever of the inhaler, wherein the lever is configured to advance a dose of medication on a flexible strip when the lever is moved from a first position to a second position;
generate an inhalation event that indicates a flow rate of an inhalation by a user based on feedback from the sensor; and
transmit the lever actuation event and the inhalation event to an external device using the wireless communication circuit.

2. The electronics module of claim 1, wherein the lever is part of a mouthpiece cover.

3. The electronics module of claim 1, wherein actuation of the switch causes the electronics module to generate the lever actuation event.

4. The electronics module of claim 1, wherein the lever actuation event indicates a movement of the lever from first to second position to advance the dose of medication on the flexible strip.

5. The electronics module of claim 1, wherein the electronics module is configured to reside in an initial off state prior to first use of the electronics module by the user, and wherein the electronics module is configured to exit the initial off state in response to a first actuation of the switch.

6. The electronics module of claim 1, wherein the electronics module is configured to periodically cause the wireless communication circuit to send advertising packets that indicate that data is stored on the electronics module when the electronics module is in the sleep state.

7. The electronics module of claim 1, further comprising:
a light-emitting diode (LED), wherein the processor is configured illuminate the LED to indicate the recording of an inhalation event by the electronics module.

8. The electronics module of claim 7, wherein the processor is configured to flash the LED to indicate the recording of the inhalation event by the electronics module.

9. The electronics module of claim 1, wherein the processor is configured to power the sensor and the wireless communication circuit in response to an actuation of the lever of the inhaler.

10. The electronics module of claim 1, wherein the processor is configured to determine inhalation parameters based on the feedback received from the sensor, wherein the inhalation parameters comprises a peak flow rate, a time to peak flow rate, an inhaled volume, and an inhalation duration, and wherein the inhalation event comprises the inhalation parameters.

11. The electronics module of claim 1, wherein the electronics module is configured to store a timeout event and associated timestamp when the lever is moved from the first position to the second position and the feedback from the sensor does not indicate an inhalation event within a predetermined amount of time.

12. The electronics module of claim 1, wherein the electronics module is configured to change from an active state to a sleep state or an off state at a predetermined time after the lever actuation event is recorded.

13. The electronics module of claim 1, wherein the lever of the inhaler is configured to advance multiple flexible strips of medication when the lever moves from the first position to the second position so that medication from each of the flexible strips are made available to the user through the mouthpiece, wherein each flexible strip includes a different medication.

14. The electronics module of claim 1, wherein the processor is configured to:
generate an exhalation event based on feedback from the sensor, wherein the exhalation event indicates that the user exhaled through the inhaler; and
transmit the exhalation event to the external device using the wireless communication circuit.

15. A method performed by an electronics module for an inhaler, the method comprising:
causing an electronics module to transition from a sleep state to an active state in response to actuation of a switch, wherein the electronics module is configured to provide power to a wireless communication circuit and the switch when in the sleep state, and wherein the electronics module is configured to provide power to a sensor, a processor and the wireless communication circuit when in the active state;
generating a lever actuation event in response to actuation of a lever of the inhaler, wherein the lever is configured to advance a dose of medication on a flexible strip when the lever is moved from a first position to a second position;
generating an inhalation event that indicates a flow rate of an inhalation by a user based on feedback from the sensor; and
transmitting the lever actuation event and the inhalation event to an external device using the wireless communication circuit.

16. The method of claim 15, wherein the lever actuation event indicates a movement of the lever from first to second position to advance the dose of medication on the flexible strip.

17. The method of claim 15, further comprising:
determining inhalation parameters based on the feedback received from the sensor, wherein the inhalation parameters comprises a peak flow rate, a time to peak flow rate, an inhaled volume, and an inhalation duration, and wherein the inhalation event comprises the inhalation parameters.

18. The method of claim 15, further comprising:
illuminating a light emitting diode (LED) of the electronics module to indicate the recording of an inhalation event by the electronics module.

19. The method of claim 15, further comprising:
storing a timeout event and associated timestamp when the lever is moved from the first position to the second position and the feedback from the sensor does not indicate an inhalation event within a predetermined amount of time.

20. The method of claim 15, wherein the lever of the inhaler is configured to advance multiple flexible strips of medication when the lever moves from the first position to the second position so that medication from each of the flexible strips are made available to the user through the mouthpiece, wherein each flexible strip includes a different medication.

\* \* \* \* \*